_(12)_ United States Patent
Brewster et al.

(10) Patent No.: US 8,008,487 B2
(45) Date of Patent: *Aug. 30, 2011

(54) SUBSTITUTED THIENO[2,3-D]PYRIMIDINES AS FUNGICIDES

(75) Inventors: William Kirkland Brewster, Indianapolis, IN (US); Carla Jean Rasmussen Klittich, Zionsville, IN (US); Terry William Balko, Greenfield, IN (US); Nneka Tuere Breaux, Indianapolis, IN (US); William Randal Erickson, Carmel, IN (US); James Edward Hunter, Indianapolis, IN (US); Christian Thomas Lowe, Westfield, IN (US); Michael John Ricks, Zionsville, IN (US); Thomas Lyman Siddall, Zionsville, IN (US); Carla Nanette Yerkes, Crawfordsville, IN (US); Yuanming Zhu, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 465 days.

This patent is subject to a terminal disclaimer.

(21) Appl. No.: 11/256,117

(22) Filed: Oct. 21, 2005

(65) Prior Publication Data

US 2006/0089370 A1    Apr. 27, 2006

Related U.S. Application Data

(60) Provisional application No. 60/621,577, filed on Oct. 21, 2004.

(51) Int. Cl.
| | |
|---|---|
| C07D 495/04 | (2006.01) |
| C07D 519/00 | (2006.01) |
| A01N 43/90 | (2006.01) |
| A01N 43/48 | (2006.01) |
| A01N 43/10 | (2006.01) |

(52) U.S. Cl. ................................ 544/278; 504/241
(58) Field of Classification Search ............... 544/117, 544/278; 504/241
See application file for complete search history.

(56) References Cited

U.S. PATENT DOCUMENTS

| | | | |
|---|---|---|---|
| 4,146,716 A | 3/1979 | Cox et al. | |
| 4,196,207 A | 4/1980 | Webber et al. | |
| 5,141,941 A | 8/1992 | Fujii et al. | |
| 5,654,307 A | 8/1997 | Bridges et al. | |
| 5,668,140 A * | 9/1997 | Schaper et al. | 514/269 |
| 6,232,320 B1 * | 5/2001 | Stewart et al. | 514/301 |
| 2003/0153556 A1 * | 8/2003 | Levy et al. | 514/218 |
| 2005/0026935 A1 * | 2/2005 | Ford et al. | 514/260.1 |

FOREIGN PATENT DOCUMENTS

| | | | |
|---|---|---|---|
| CA | 2038521 | | 9/1991 |
| DE | 26 54 090 | | 6/1977 |
| EP | 447891 | * | 3/1991 |
| EP | 424 125 | | 4/1991 |
| EP | 0 447 891 | | 4/1994 |
| GB | 2 043 061 | | 10/1980 |
| JP | 3063266 | | 3/1991 |
| JP | 2762430 | | 8/1992 |
| JP | 1995010712 | | 1/1995 |
| WO | WO 2004092123 | * | 10/2004 |

OTHER PUBLICATIONS

Jordis et. al. (Vestnik Slovenskega Kemijskega Drustva, 1986, 33(3), 217-238).*
Michael Berger, et al; S(+)-4-(1-Phenylethylamino)quinazolines as Inhibitors of Human Immunoglobuline E Synthesis: Potency Is Dictated by Sterochemistry and Atomic Point Charges at N-1; Journal of Medical Chemistry 2001; 44, pp. 3031-3038.
Yoshinori Yamanaka, et al; Quantitative structure-fungicidal activity relationships of N-(4-difluoromethoxybenzyl)-pyrimidin-4-amines against wheat and barley fungi; Pesticide Science, 55:896-902 (1999).

* cited by examiner

*Primary Examiner* — Susanna Moore
(74) *Attorney, Agent, or Firm* — Charles W. Arnett

(57) ABSTRACT

The present invention provides compounds of formula (I), thieno[2,3-d]pyrimidines, having fungicidal activity.

(I)

2 Claims, No Drawings

SUBSTITUTED THIENO[2,3-D]PYRIMIDINES AS FUNGICIDES

CROSS-REFERENCE TO RELATED APPLICATIONS

This application claims the benefit of U.S. Provisional Patent Application Ser. No. 60/621,577, filed Oct. 21, 2004, which is expressly incorporated by reference herein.

This invention is related to the field of thieno-pyrimidine compounds having fungicidal activity.

Fungicides are compounds, of natural or synthetic origin, which act to protect plants against damage caused by fungi. However, no one fungicide is useful in all situations. Consequently, research is being conducted to produce fungicides that have better performance, are easier to use, and that cost less.

DE 2,654,090 and U.S. Pat. No. 4,146,716, incorporated herein by reference, disclose thieno-pyrimidine compounds useful for controlling fungal, viral and bacterial plant diseases. U.S. Pat. No. 4,196,207, incorporated herein by reference discloses similar compounds useful in controlling infestations of ticks on animals. CA 2,038,521 and EP-447,891 disclose thieno-pyrimidine derivatives useful as insecticides, growth regulators and herbicides. GB2043061 discloses thienopyrimidine derivatives as plant fungicidal, bactericidal, antiviral, insecticidal and growth regulating compounds. Other references which teach various thieno-pyrimidine compounds for fungicidal use include JP1995010712, JP03063266, EP-424125, and U.S. Pat. No. 5,141,941 (incorporated herein by reference). Pharmaceutical uses of thieno-pyrimidines have also been disclosed in U.S. Pat. No. 5,654,307 (incorporated herein by reference).

However, there remains a need to develop additional thieno-pyrimidine compounds useful as fungicides.

The present invention relates to thieno-pyrimidines, particularly thieno[2,3-d]pyrimidines and their use as fungicides. The compounds of the present invention offer protection against ascomycetes, basidiomycetes, deuteromycetes and oomycetes.

The present invention relates to compounds having the Formula (I):

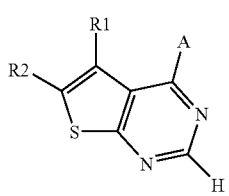

Wherein each R1 is independently selected from H, Cl, Br, F, I, $C_1$-$C_8$ alkoxy, hydroxy, cyano, carbonylalkoxy (COOR), thioalkyl, and sulfonylalkyl ($SO_2R$);

R2 is independently selected from H, Cl, Br, F, I, $C_1$-$C_8$ alkyl, $C_3$-$C_8$ alkenyl, $C_3$-$C_8$ alkynyl, nitro, and carbonylalkoxy(COOR), with the proviso that R1 and R2 are not both H;
but, preferably at least one of R1 or R2 is H;

A is selected from:
1) NH—R"

wherein R" is selected from the rings:

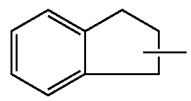

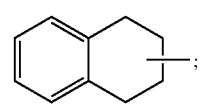

2) i) 1,3-Dihydro-2H-isoindol-2-yl or
ii) a N-containing mono or bicyclic ring structure containing from 1-3 total heteroatoms,
wherein the N-containing mono or bicyclic ring is substituted with $C_1$-$C_8$ alkyl, $C_3$-$C_8$ alkenyl, $C_3$-$C_8$ alkynyl, halo, or another mono or bicyclic ring containing from 0-3 heteroatoms;
wherein the point of attachment is the N atom of the N-containing ring; or
3) —NH—Y—R*
wherein Y is a linking group selected from the group consisting of $C_1$-$C_8$ alkyl, $C_3$-$C_8$ alkenyl, or $C_3$-$C_8$ alkynyl, optionally substituted with hydroxy, alkoxy, $C_1$-$C_8$ alkylether, and/or phenyl; and
R* is selected from
a) a mono or bicyclic ring optionally containing from 0-3 heteroatoms selected from the group consisting of
a1) phenyl
a2) oxazolyl
a3) furanyl
a4) thiazolyl
a5) naphthyl
a6) pyrimidinyl
a7) cyclopropyl
a8) pyridinyl
a9) benzothiazolyl
a10) benzodioxolyl
a11) pyrrolyl
a12) benzoxazolyl
a13) pyrazinyl
a14) thienyl
b) $C_1$-$C_8$ alkyl, $C_3$-$C_8$ alkenyl, $C_3$-$C_8$ alkynyl,
c) $C_1$-$C_8$ alkoxy,
d) substituted or unsubstituted O-pyridinyl, or
e) phenoxy;
wherein R* can be additionally substituted with one or more R* substituents selected from the group consisting of alkoxycarbonyl (—C(O)OR), —R, —ROR, —OCH$_2$C(O)R, —OC(O)R, —N—C(O)OR, (wherein R is $C_1$-$C_8$ alkyl, $C_3$-$C_8$ alkenyl, $C_3$-$C_8$ alkynyl or $C_5$-$C_6$ cycloalkyl), halogen, haloalkoxy, alkoxy, benzyloxy, phenoxy, haloalkyl, pyridinyl, phenoxyalkoxy, benzyloxyalkoxy, haloalkylether, oxazolyl, furanyl, thiazolyl, naphthyl, pyrimidinyl, cyclopropyl, benzothiazolyl, benzoxazolyl, benzodioxolyl, morpholinyl, formamido (—NCHO), unsubstituted thioalkyl, and acetamido (—NC(O)R);
wherein the R* substituents listed above, if substituted, are substituted with haloalkoxy, haloalkyl, alkoxy, halo, $C_1$-$C_8$ alkyl, $C_3$-$C_8$ alkenyl, $C_3$-$C_8$ alkynyl, or benzyloxy;

with the provisos that:
1) when Y is
   i) unsubstituted alkyl or
   ii) alkyl substituted with unsubstituted phenyl,
   and R1 is Cl,
   then R* is not
   i) unsubstituted phenyl,
   ii) monosubstituted halophenyl or alkoxyphenyl, or
   iii) disubstituted phenyl wherein both substituents are alkoxy;
2) when Y is unsubstituted alkyl
   and R* is phenyl monosubstituted with alkoxy,
   then neither R1 or R2 are Cl;
3) when Y is alkyl, alkenyl, alkynyl or alkylhydroxy,
   and R1 is Cl,
   then R* cannot be unsubstituted alkyl, alkenyl or alkynyl;
4) when Y is unsubstituted alkyl
   and R1 is Cl,
   then R* cannot be furanyl, unsubstituted phenoxy, unsubstituted pyridinyl, methyl substituted pyridinyl, chloro substituted pyridinyl, unsubstituted thienyl; 4[4-fluorophenoxy]-tetrafluorophenyl, pentafluoro phenoxy phenyl, or difluorobenzodioxole (where F is substituted in the hetero ring);
5) when Y is alkyl substituted with methoxyphenyl and R1 is Cl,
   then R* cannot be methoxyphenyl.

Within the present specification, the term "halogen" or "halo" refers to one or more halogen atoms, defined as F, Cl, Br, and I. The term "alkyl" refers to an unbranched, or branched, carbon chain having from 1 to 8 carbon atoms ($C_1$-$C_8$ alkyl) unless specified otherwise, including methyl, ethyl, propyl, butyl, isopropyl, isobutyl, tertiary butyl, pentyl, hexyl and the like, preferably from 1 to 6 carbon atoms ($C_1$-$C_6$ alkyl). The term "unsubstituted alkyl" refers to a branched or straight chain alkyl group which does not contain any other functional groups other than alkyl. The term "alkenyl", or "alkynyl" refers to an unbranched, or branched, carbon chain having from 3 to 8 carbon atoms, including ethenyl, propenyl, butenyl, isopropenyl, isobutenyl, propynyl, butynyl and the like, preferably from 3 to 6 carbon atoms ($C_3$-$C_6$). As used throughout this specification, the term 'R' refers to the group consisting of $C_{1-8}$ alkyl, $C_{3-8}$ alkenyl or $C_{3-8}$ alkynyl, unless stated otherwise. The term "haloalkyl" refers to an alkyl, alkenyl or alkynyl group which is substituted with Cl, F, I, or Br. The term "alkylether" refers to an —ROR substituent. The term "alkylcarbonyl" refers to a —C(=O)R substituent. The term "alkoxy" refers to an —OR substituent wherein R is an unbranched or branched alkyl carbon chain, including methyl, ethyl, propyl, butyl, isopropyl, isobutyl, tertiary butyl, pentyl, hexyl, and the like, preferably a $C_1$-$C_4$ carbon chain. The term "hydroxy" refers to an —OH group. The term "haloalkoxy" refers to a —OR—X group, wherein R may be substituted with X based on the formula $R=C_nH_{(2n+1)-y}X_y$, wherein X is Cl, F, Br, or I, or any combination thereof and y is an integer from 0 to 2n+1. The term "benzyloxy" refers to an O—$CH_2$Ph substituent, wherein Ph is phenyl or substituted phenyl. The term "phenoxy" refers to an —OPh substituent, wherein Ph is a substituted or unsubstituted phenyl group. The term "alkoxycarbonyl" refers to a —C(=O)—OR substituent. The term "aryl" refers to a phenyl or substituted phenyl group. The term "alkylthio" refers to a —S—R group. The term "alkylsulfonyl" refers to an —$SO_2$—R group wherein R is alkyl. The term "—O-pyridinyl" refers to an oxygen bonded to a pyridine ring. The term "formamido" refers to a —NCHO group. The term "acetamido" refers to a —NCOR group. The term "alkoxyphenoxy" refers to a phenoxy group, additionally substituted with an alkoxy group (—O-Ph-OR). The term "alkoxybenzyloxy" refers to a —$OCH_2$Ph-O—R group. The term "haloalkylether" refers to an alkylether group which is substituted with a Cl, F, Br, or I substituent.

A mono or bicyclic ring structure containing from 0-3 heteroatoms includes any aromatic or non-aromatic $C_3$ to $C_{10}$ mono or bicyclic ring structure, optionally containing up to 3 heteroatoms. Monocyclic rings include aromatic and nonaromatic rings having 5 or 6 members, optionally containing N, S and/or O; wherein bicyclic rings include aromatic or non-aromatic bicyclic fused rings optionally containing N, S and/or O. Examples of such rings include phenyl, naphthyl, tetrahydronaphthyl, indanyl, indenyl, cyclohexyl, cyclopentyl, cyclopropyl, cyclobutyl, cyclopentenyl, piperidinyl, piperazinyl, pyrrolidinyl, tetrahydrothienyl, morpholinyl, indolyl, benzoxazolyl, benzothiazolyl, hydrobenzodioxolyl, oxazolyl, furanyl, thiazolyl, pyridinyl, pyrimidinyl, triazinyl, thiophenyl, benzodioxolyl, pyrazolyl, benzimidazolyl, pyrazolinyl, pyranyl, pyridazinyl, pyrrolyl, thiazolinyl, imidazolyl, pyrazinyl and the like.

A N-containing mono or bicyclic ring structure containing from 1-3 total heteroatoms includes any aromatic or non-aromatic $C_4$-$C_8$ mono or bicyclic ring structure containing N and up to two additional heteroatoms. Examples of such rings include piperidinyl, pyrrolidinyl, morpholinyl, indolyl, benzoxazolyl, benzothiazolyl, oxazolyl, thiazolyl, pyridinyl, pyrimidinyl, triazinyl, pyrazolyl, pyrazolinyl, pyridazinyl, pyrrolyl, thiazolinyl, imidazolyl, pyrazinyl and the like.

While all the compounds of the present invention have fungicidal activity, certain classes of compounds may be preferred for reasons such as, for example, greater efficacy, reduced toxicity or ease of synthesis.

Throughout the specification, reference to the compounds of Formula I is read as also including optical isomers and salts of Formula I, and hydrates thereof. Specifically, when Y is a branched chain alkyl group, it is understood that such compounds include optical isomers and racemates thereof. Exemplary salts include: hydrochloride, hydrobromide, hydroiodide, and the like.

In one embodiment, the compounds of the present invention are those represented by Formula I wherein:
R1 is Cl, Y is unsubstituted alkyl, and R* is substituted phenyl, wherein the phenyl is substituted with at least one group (substituent) selected from:
  carbonylalkoxy (—C(O)OR), —R, —ROR, (wherein each R is $C_1$-$C_8$ alkyl, $C_3$-$C_8$ alkenyl, $C_3$-$C_8$ alkynyl or $C_5$-$C_6$ cycloalkyl), haloalkyl, phenoxy, benzyloxy, formamido (—NCHO), unsubstituted alkylthio, acetamido (—NC(O)R);
  or is disubstituted with the proviso that both substituents are not alkoxy and preferably one substituent is alkoxy and one is either $C_1$-$C_8$ alkyl or halo;
wherein the substituents of the phenyl ring listed above may be additionally substituted. Examples of such additional substituents include haloalkoxy, haloalkyl, alkoxy, halo, $C_1$-$C_8$ alkyl, $C_3$-$C_8$ alkenyl, $C_3$-$C_8$ alkynyl, and benzyloxy.

It is also understood by those skilled in the art that additional substitution is allowable, as long as the rules of chemical bonding and strain energy are satisfied and the product still exhibits adequate fungicidal activity.

Another embodiment of the present invention is a use of a compound of Formula I, for protection of a plant against attack by a phytopathogenic organism or the treatment of a plant infested by a phytopathogenic organism, comprising applying a compound of Formula I, or a composition comprising said compound to soil, a plant, a part of a plant, foliage, and/or seeds.

Additionally, another embodiment of the present invention is a composition useful for protecting a plant against attack by a phytopathogenic organism and/or treatment of a plant infested by a phytopathogenic organism comprising a compound of Formula I and a phytologically acceptable carrier material.

The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates.

Preferably, the compounds of the present invention are applied in the form of a formulation, comprising one or more of the compounds of Formula I with a phytologically acceptable carrier. Concentrated formulations can be dispersed in water, or other liquids, for application, or formulations can be dust-like or granular, which can then be applied without further treatment. The formulations can be prepared according to procedures that are conventional in the agricultural chemical art.

The present invention contemplates all vehicles by which one or more of the compounds can be formulated for delivery and use as a fungicide. Typically, formulations are applied as aqueous suspensions or emulsions. Such suspensions or emulsions are produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds can be added may be used, provided they yield the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder is usually from 10 percent to 90 percent by weight based on the total weight of the wettable powder, more preferably 25 wt. percent to 75 wt. percent. In the preparation of wettable powder formulations, the compounds can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I comprise a convenient concentration, such as from 10 wt. percent to 50 wt. percent of the compound, in a suitable liquid, based on the total weight of the concentrate. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which can be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Preferred organic liquids include xylene, and propyl benzene fractions, with xylene being most preferred. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from 5 to 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds of Formula I can also be applied as granular formulations, which are particularly useful for applications to the soil. Granular formulations usually contain from 0.5 to 10 wt. percent, bases on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from 0.5 to 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I can be prepared by intimately mixing one or more of the compounds in powdered form with a suitable dusty agricultural carrier, such as, for example, kaolin clay, ground volcanic rock, and the like. Dusts can suitably contain from 1 to 10 wt. percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to, ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that contain other pesticidal compounds. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I, and the pesticidal compound in the combination can generally be present in a weight ratio of from 1:100 to 100:1.

Another embodiment of the present invention is a method for the control or prevention of fungal attack. This method comprises applying to the soil, plant, roots, foliage, seed or locus of the fungus, or to a locus in which the infestation is to be prevented (for example applying to cereal or grape plants), a fungicidal effective amount of one or more of the compounds. The compounds are suitable for treatment of various plants at fungicidal levels, while exhibiting low phytotoxicity. The compounds are useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from 0.1 to 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from 0.10 to 4 pounds/acre (0.01 to 0.45 grams per square meter, $g/m^2$).

Any range or desired value given herein may be extended or altered without losing the effects sought, as is apparent to the skilled person for an understanding of the teachings herein.

The compounds of the present invention are prepared in general by the reaction of an appropriate thieno-pyrimidine with one to four equivalents of an appropriate amine or its hydrochloride salt, with an excess of base in a suitable inert solvent, under conditions such that the desirable amine substituted thieno-pyrimidine is obtained. Examples of bases include, but are not limited to: pyridine, triethylamine, potassium carbonate, and the like. Examples of solvents include, but are not limited to: pyridine, dimethyl formamide (DMF), dimethylsulfoxide (DMSO), ethanol, tetrahydrofuran (THF), dichloromethane and the like. In general, the reaction is carried out at temperatures from 20 to 150° C. depending upon the method utilized.

The amines used to prepare the compounds of the present invention are commercially available, known in the literature, or are prepared by a number of means which include, but are not limited to, the following procedures:

Method A: Conversion of a ketone to the corresponding imine and reduction in situ with sodium borohydride in the presence of titanium (IV) isopropoxide as taught in Miriyala, B.; Bhattacharyya, S.; Williamson, J. S. *Tetrahedron Lett.* 2004, 60, 1463.

Method B: Conversion of a ketone to the corresponding imine and reduction in situ with sodium borohydride in the presence of zirconium tetrachloride as taught in Itsuno, S.; Sakurai, Y.; Ito, K. *Synthesis* 1988, 995.

Method C: Conversion of a ketone to its corresponding imine and reduction in situ with sodium cyanoborohydride as taught in Williams, R. M.; Ehrlich, P. P.; Zhu, W.; Hendrix, J. *J. Org. Chem.* 1987, 52, 2615.

Method D: Conversion of a ketone to its corresponding hydroxime or methoxime as described in Moffett, R. B.; Robert, A.; Schumann, E. L.; Paquette, L. A. *J. Heterocyclic Chem.* 1979, 16, 1459, with subsequent reduction with hydrogen gas in the presence of Raney nickel as taught in Baker, W. R.; Conden, S. L. *J. Org. Chem.* 1993, 58, 3277.

Method E: Conversion of a ketone to its corresponding methoxime as described in Moffett, R. B.; Robert, A.; Schumann, E. L.; Paquette, L. A. *J. Heterocyclic Chem.* 1979, 16, 1459, with subsequent reduction with hydrogen gas in the presence of palladium on carbon.

Method F: Conversion of a ketone to its corresponding methoxime as described in Moffett, R. B.; Robert, A.; Schumann, E. L.; Paquette, L. A. *J. Heterocyclic Chem.* 1979, 16, 1459, with subsequent reduction with hydrogen gas generated in situ from ammonium formate in the presence of palladium on carbon as described in Jnaneshwara, G. K.; Sudalai, A.; Deshpande, V. H. *J. Chem. Res., Synopses* 1998, 3, 160.

Method G: Conversion of a ketone to its corresponding methoxime as described in Moffett, R. B.; Robert, A.; Schumann, E. L.; Paquette, L. A. *J. Heterocyclic Chem.* 1979, 16, 1459, with subsequent reduction with borane THF complex.

Method H: Reduction of a nitrile to its corresponding amine as described in Frejd, T.; Klingstedt, T. *Synthesis* 1987, 1, 40.

The amines prepared by these methods are tabulated in Table 1. The racemic amine mixture (compound 95) was separated into pure enantiomers (compound 112 and compound 113) via their mandelate salts as described in Saigo, K.; Kai, M.; Yonezawa, N.; Hasegawa, M. *Synthesis* 1985, 2, 214-16.

The ketones and nitrites used in these amine preparations are commercially available, known in the literature, or prepared as described in the Examples.

TABLE 1

| Compound No. | Amine | Reduction Method | Compound No. | Starting Ketone or Nitrile |
|---|---|---|---|---|
| 95 | | F | 152 | |
| 96 | | G | 153 | |
| 97 | | H | 154 | |
| 98 | | B | 155 | |
| 99 | | B | 156 | |
| 100 | | H | 157 | |

TABLE 1-continued

| Compound No. | Amine | Reduction Method | Compound No. | Starting Ketone or Nitrile |
|---|---|---|---|---|
| 101 | H₂N-CH₂CH₂-C₆H₄-CH(CH₃)₂ (2-(4-isopropylphenyl)ethylamine) | H | 158 | NC-CH₂-C₆H₄-CH(CH₃)₂ (4-isopropylphenylacetonitrile) |
| 102 | 1-(1H-pyrrol-2-yl)ethylamine | E | 159 | 1-(1H-pyrrol-2-yl)ethanone |
| 103 | 1-(1-methyl-1H-pyrrol-3-yl)ethylamine | E | 160 | 1-(1-methyl-1H-pyrrol-3-yl)ethanone |
| 104 | 1-(1-methyl-1H-pyrrol-2-yl)ethylamine | E | 161 | 1-(1-methyl-1H-pyrrol-2-yl)ethanone |
| 105 | 1-(4-(methoxymethyl)phenyl)ethylamine | E | 162 | 1-(4-(methoxymethyl)phenyl)ethanone |
| 106 | 1-(1H-pyrrol-3-yl)ethylamine | E | 163 | 1-(1H-pyrrol-3-yl)ethanone |
| 107 | 1-(1-isopropyl-1H-pyrrol-3-yl)ethylamine | E | 164 | 1-(1-isopropyl-1H-pyrrol-3-yl)ethanone |
| 108 | 1-(5-(trifluoromethyl)pyridin-2-yl)ethylamine | E | 165 | 1-(5-(trifluoromethyl)pyridin-2-yl)ethanone |
| 109 | 1-(oxazol-5-yl)ethylamine | — | — | see text |

TABLE 1-continued

| Compound No. | Amine | Reduction Method | Compound No. | Starting Ketone or Nitrile |
|---|---|---|---|---|
| 110 | 1-(thiazol-2-yl)ethylamine | E | 166 | 1-(thiazol-2-yl)ethanone |
| 111 | 1-(pyrazin-2-yl)ethylamine | see text | 167 | 1-(pyrazin-2-yl)ethanone |
| 112 | (+)-1-(4-isopropylphenyl)ethylamine | E, then resolution | 152 | 1-(4-isopropylphenyl)ethanone |
| 113 | (−)-1-(4-isopropylphenyl)ethylamine | E, then resolution | 152 | 1-(4-isopropylphenyl)ethanone |
| 114 | 1-(4-trifluoromethylphenyl)ethylamine | F | 168 | 1-(4-trifluoromethylphenyl)ethanone |
| 115 | 1-(5-methoxypyridin-2-yl)ethylamine | F | 169 | 1-(5-methoxypyridin-2-yl)ethanone |
| 116 | 1-(6-chloropyridin-3-yl)ethylamine | C | 170 | 1-(6-chloropyridin-3-yl)ethanone |
| 117 | 1-(6-methoxypyridin-3-yl)ethylamine | C | 171 | 1-(6-methoxypyridin-3-yl)ethanone |

TABLE 1-continued

| Compound No. | Amine | Reduction Method | Compound No. | Starting Ketone or Nitrile |
|---|---|---|---|---|
| 118 | 1-(5-isopropylpyridin-2-yl)ethanamine | D | 172 | 1-(5-isopropylpyridin-2-yl)ethanone |
| 119 | 1-(5-(benzyloxy)pyridin-2-yl)ethanamine | C | 173 | 1-(5-(benzyloxy)pyridin-2-yl)ethanone |
| 120 | 1-(5-methoxypyrimidin-2-yl)ethanamine | D | 174 | 1-(5-methoxypyrimidin-2-yl)ethanone |
| 121 | 1-(6-(2,2,2-trifluoroethoxy)pyridin-3-yl)ethanamine | D | 175 | 1-(6-(2,2,2-trifluoroethoxy)pyridin-3-yl)ethanone |
| 122 | 1-(6-ethoxypyridin-3-yl)ethanamine | D | 176 | 1-(6-ethoxypyridin-3-yl)ethanamine |
| 123 | 1-(6-fluoropyridin-3-yl)ethanamine | B | 177 | 1-(6-fluoropyridin-3-yl)ethanone |
| 124 | 1-(benzo[d]thiazol-2-yl)ethanamine | D | 178 | 1-(benzo[d]thiazol-2-yl)ethanone |
| 125 | 1-(4-(methylthio)phenyl)ethanamine | D | 179 | 1-(4-(methylthio)phenyl)ethanone |

TABLE 1-continued

| Compound No. | Amine | Reduction Method | Compound No. | Starting Ketone or Nitrile |
|---|---|---|---|---|
| 126 | H2N-CH(CH3)-[5-(6-CF3)pyridyl] | D | 180 | CH3-C(O)-[5-(6-CF3)pyridyl] |
| 127 | H2N-CH(CH3)-CH2-O-[5-(6-OMe)pyridyl] | A | 181 | CH3-C(O)-CH2-O-[5-(6-OMe)pyridyl] |
| 128 | H2N-CH(CH3)-[5-(2-OCH2CF3)pyrimidyl] | A | 182 | CH3-C(O)-[5-(2-OCH2CF3)pyrimidyl] |
| 129 | H2N-CH(CH3)-[5-(2-OMe)pyrimidyl] | D | 183 | CH3-C(O)-[5-(2-OMe)pyrimidyl] |
| 130 | H2N-CH(CH3)-CH2-O-[6-Cl-2-pyridyl] | — | — | see text |
| 131 | H2N-CH(CH3)-[4-(NHCHO)phenyl] | D | 184 | CH3-C(O)-[4-(NHCHO)phenyl] |
| 132 | H2N-CH(CH3)-[4-(NHC(O)CH3)phenyl] | D | 185 | CH3-C(O)-[4-(NHC(O)CH3)phenyl] |
| 133 | H2N-CH(CH3)-[3,4-methylenedioxyphenyl] | D | 186 | CH3-C(O)-[3,4-methylenedioxyphenyl] |
| 134 | H2N-CH(CH2OMe)-phenyl | A | 187 | MeO-CH2-C(O)-phenyl |

TABLE 1-continued

| Compound No. | Amine | Reduction Method | Compound No. | Starting Ketone or Nitrile |
|---|---|---|---|---|
| 135 | 1-(4-methoxy-3-methylphenyl)ethylamine | D | 188 | 1-(4-methoxy-3-methylphenyl)ethanone |
| 136 | 2-(6-chloropyridin-3-yl)ethylamine | H | 189 | (6-chloropyridin-3-yl)acetonitrile |
| 137 | 1-(3-fluoro-4-methoxyphenyl)ethylamine | D | 190 | 1-(3-fluoro-4-methoxyphenyl)ethanone |
| 138 | 1-(3-chloro-4-methoxyphenyl)ethylamine | D | 191 | 1-(3-chloro-4-methoxyphenyl)ethanone |
| 139 | 1-(2-methoxythiazol-5-yl)ethylamine | A | 192 | 1-(2-methoxythiazol-5-yl)ethanone |
| 140 | 1-(4-(2,2,2-trifluoroethoxy)phenyl)ethylamine | A | 193 | 1-(4-(2,2,2-trifluoroethoxy)phenyl)ethanone |
| 141 | 1-(4-(2,2-difluoroethoxy)phenyl)ethylamine | A | 194 | 1-(4-(2,2-difluoroethoxy)phenyl)ethanone |
| 142 | 1-(6-(2-fluoroethoxy)pyridin-3-yl)ethylamine | A | 195 | 1-(6-(2-fluoroethoxy)pyridin-3-yl)ethanone |
| 143 | 1-(6-methoxypyridin-3-yl)propylamine | A | 196 | 1-(6-methoxypyridin-3-yl)propan-1-one |

TABLE 1-continued

| Compound No. | Amine | Reduction Method | Compound No. | Starting Ketone or Nitrile |
|---|---|---|---|---|
| 144 | 1-(2-chloropyridin-3-yl)ethan-1-amine | A | 197 | 1-(2-chloropyridin-3-yl)ethan-1-one |
| 145 | 1-(2-(methoxymethyl)cyclopropyl)ethan-1-amine | A | 198 | 1-(2-(methoxymethyl)cyclopropyl)ethan-1-one |
| 146 | 1-(4-(trifluoromethoxy)phenyl)ethan-1-amine | A | 199 | 1-(4-(trifluoromethoxy)phenyl)ethan-1-one |
| 147 | 1-(4-fluoro-2-methoxyphenyl)ethan-1-amine | A | 200 | 1-(4-fluoro-2-methoxyphenyl)ethan-1-one |
| 148 | 1-(2-(((4-methoxybenzyl)oxy)methyl)cyclopropyl)ethan-1-amine | A | 201 | 1-(2-(((4-methoxybenzyl)oxy)methyl)cyclopropyl)ethan-1-one |
| 149 | 1-(2-(((4-methoxyphenoxy)methyl)cyclopropyl)ethan-1-amine | A | 202 | 1-(2-(((4-methoxyphenoxy)methyl)cyclopropyl)ethan-1-one |
| 150 | 1-(2-((2,2,2-trifluoroethoxy)methyl)cyclopropyl)ethan-1-amine | A | 203 | 1-(2-((2,2,2-trifluoroethoxy)methyl)cyclopropyl)ethan-1-one |
| 151 | 1-(2-(2,2,2-trifluoroethoxy)thiazol-5-yl)ethan-1-amine | A | 204 | 1-(2-(2,2,2-trifluoroethoxy)thiazol-5-yl)ethan-1-one |
| 205 | 2-(4-(2-oxopropoxy)phenyl)ethan-1-amine | none | — | see text |
| 206 | 2-(4-morpholinophenyl)ethan-1-amine | none | — | see text |

TABLE 1-continued

| Compound No. | Amine | Reduction Method | Compound No. | Starting Ketone or Nitrile |
|---|---|---|---|---|
| 207 | Me-CH(NH₂)-C₆H₄-N(morpholine) | A | 208 | Me-C(=O)-C₆H₄-N(morpholine) |

The following examples are provided to further illustrate the invention. They are not meant to be construed as limiting the invention.

EXAMPLES

Preparation of the Thieno-Pyrimidines of the Present Invention

Example 1

(5-Chlorothieno[2,3-d]pyrimidin-4-yl)-[1-(4-isopropylphenyl)ethyl]amine (Compound 1)

A mixture of 4,5-dichlorothieno[2,3-d]pyrimidine (prepared as taught in EP 447,891) (775 mg, 3.8 mmol), 1-(4-isopropylphenyl)ethanamine (compound 95) (734 mg, 4.5 mmol), and triethylamine (767 mg, 7.6 mmol) in DMF (20 mL) was allowed to react for 24 hours at 20° C. The reaction mixture was diluted with water and extracted thrice with Et₂O. The organic portions were combined, washed with brine, and dried (Na₂SO₄). The mixture was filtered through silica gel, and the solvent was removed in vacuo. The residue was purified by flash chromatography (15 percent Et₂O in pentane), yielding 1.1 g of oil.

Examples 2-17

These examples were prepared by the process of Example 1 using the appropriate amine.

Example 18

5-chloro-N-(1-methyl-2-{[5-(trifluoromethyl)pyridin-2-yl]oxy}ethyl)thieno [2,3-d]pyrimidin-4-amine (compound 18) A mixture of 2-fluoro-5-(trifluoromethyl)pyridine (142 mg), 2-[(5-chlorothieno[2,3-d]pyrimidinyl-4)amino]-1-propanol, (compound 94) (0.2 g) and 1M THF solution of potassium t-butoxide (1.0 mL) in DMSO (10 mL) was stirred at approximately 25° C. for 72 hours. The mixture was diluted with Et₂O and washed with H₂O and brine. The organic phase was then dried (Na₂SO₄) and filtered through silica gel. Solvent was removed in vacuo and the residue was purified via flash chromatography, yielding 118 mg of oil.

Examples 19-36

These examples were prepared by the process of Example 1 using the appropriate amine.

Example 37

5-(chlorothieno[2,3-d]pyrimidin-4-yl)-[1-methyl-2-(pyridin-2-yloxy)ethyl]amine (Compound 37)

This example was prepared using 2-fluoropyridine according to the procedure of Example 18.

Examples 38-42

These examples were prepared by the process of Example 1 using the appropriate amine.

Example 43

(S)-5-Ethoxythieno[2,3-d]pyrimidin-4-yl)-[1-(4-methoxyphenyl)ethyl]amine (compound 43) A mixture of 5-ethoxy-4-chlorothieno[2,3-d]pyrimidine (163 mg, 0.76 mmol) and (S)-1-(4-methoxyphenyl)ethylamine (120 mg, 0.79 mmol) and triethylamine (159 µL, 1.14 mmol) in DMF (2.0 mL) was allowed to react for 5 hours at 50° C. The reaction mixture was filtered through a cotton plug and purified by High Pressure Liquid Chromatography (HPLC) (Gilson system; Phenomenex column: Luna 5µ C18(2), 150×21.20 mm, 5µ micro) with a water/acetonitrile gradient. Appropriate fractions were pooled to provide 125 mg of pale yellow solid.

Preparation of 5-ethoxy-4-chlorothieno [2,3-d]pyrimidine

2-Amino-3-cyano-4-ethoxythiophene (made according the method disclosed in EP 193885) (3.5 g, 21 mmol) was dissolved in phosphorus oxychloride (20 mL, 32 g, 210 mmol, 10 eq.), cooled to 0° C. and treated dropwise with DMF (1.7 mL, 1.6 g, 22 mmol, 1.05 eq.). After the addition was complete the mixture was slowly heated to 100° C. and stirred for 2 hours. The mixture was cooled, the volatiles removed in vacuo and the residue was treated with ice-water and extracted with dichloromethane. The organic extracts were washed with water, brine, dried (Na₂SO₄) and evaporated. The residue was recrystallized from hot acetonitrile to give the purified thienopyrimidine 1.8 g (40 percent) yield.

Example 44

This example was prepared by the process of Example 1 using the appropriate amine.

Example 45

(5-Bromothieno[2,3-d]pyrimidin-4-yl)-[1-(2-methoxypyridin-5-yl)ethyl]amine (compound 45) A mixture of 5-bromo-4-chlorothieno[2,3-d]pyrimidine (279 mg, 1.1 mmol), the amine (compound 117) (256 mg, 1.7 mmol) and triethylamine (170 mg, 1.7 mmol) in DMF (3 mL) was stirred at 60° C. for 4 hours. After cooling, the mixture was diluted with water (20 mL) and extracted with ether (3×25 mL). The combined organics were dried ($Na_2SO_4$), filtered and stripped leaving product as a yellow oil, 296 mg, 74 percent yield.

Preparation of
5-Bromo-4-chlorothieno[2,3-d]pyrimidine

Lithium diisopropylamine (LDA) was prepared by addition of 2.5 molar BuLi (3.0 mL, 7.6 mmol) in hexanes to a ca. −50° C. solution of diisopropylamine (1.1 mL, 790 mg, 7.8 mmol) in anhydrous THF (15 mL). The solution was warmed to 0° C. for 10 min and then added dropwise to a solution of 6-bromo-4-chlorothieno[2,3-d]pyrimidine (which was prepared as disclosed in WO 2003053446) (2.0 g, 8.0 mmol) in THF (30 mL) cooled to −100° C. The mixture was maintained at −90 to −100° C. for 45 minutes and then quenched with saturated aqueous $NH_4Cl$. The mixture was diluted with ethyl acetate (30 mL) and the separated organic phase was washed with water, brine, dried ($Na_2SO_4$) and evaporated. The residue was recrystallized from aqueous ethanol and the isolated solid was dissolved in dichloromethane and passed through a silica gel plug eluting with dichloromethane to yield 900 mg of material. A further 200 mg of product was obtained from the evaporated, recrystallization filtrate by reverse phase High Pressure Liquid Chromatography (HPLC) on a 50 mm×250 mm YMC-AQ eluting with 70/30 acetonitrile/0.1 percent v/v water-conc. $H_3PO_4$. Total yield was 1.1 g (55 percent). In later runs the crude bromide was recrystallized from acetonitrile.

Example 46

This example was prepared as in Example 43 using the appropriate amine.

Example 47

[1-(4-Methoxyphenyl)ethyl]-(6-nitrothieno[2,3-d]pyrimidin-4-yl)amine (Compound 47)

A mixture of 4-chloro-6-nitrothieno[2,3-d]pyrimidine (prepared as disclosed in *Bull. Chim. Soc. Fr.* 1975, 3-4, Pt. 2, 592) (500 mg, 2.3 mmol), 1-(4-methoxyphenyl)ethanamine HCl (513 mg, 2.8 mmol), and triethylamine (581 mg, 5.7 mmol) in DMF (7 mL) was allowed to react for 24 hours at 20° C. The reaction mixture was diluted with water and extracted thrice into $Et_2O$. The organic portions were combined, washed with brine, and dried ($Na_2SO_4$). The mixture was filtered through silica gel, and the solvent was removed in vacuo. The residue was purified by flash chromatography (40 percent EtOAc in pentane), yielding 385 mg.

Example 48

(6-Bromothieno[2,3-d]pyrimidin-4-yl)-[1-(4-methoxyphenyl)ethyl]amine (Compound 48)

A mixture of 6-bromo-4-chlorothieno[2,3-d]pyrimidine (prepared as disclosed in WO 2003053446) (500 mg, 2.0 mmol), the amine hydrochloride (compound 117) (563 mg, 3.0 mmol) and triethylamine (505 mg, 5.0 mmol) in DMF (7 mL) was stirred at approximately 25° C. for 20 hours. After cooling, the mixture was diluted with water (20 mL) and extracted with ether (3×25 mL). The combined organics were washed with water, saturated brine, and dried ($Na_2SO_4$). Filtration and removal of solvent gave product as an off-white solid, 300 mg, 0.83 mmol, 41 percent yield.

Example 49

5-Cyano-N-[1-(4-methoxyphenyl)ethyl]thieno[2,3-d]pyrimidin-4-amine (Compound 49)

5-Bromo-N-[1-(4-methoxyphenyl)ethyl]thieno[2,3-d]pyrimidin-4-amine (250 mg, 0.69 mmol) and cuprous cyanide (310 mg, 3.4 mmol, 5 eq.) were combined in dry N-methylpyrrolidinone (NMP) (4 mL) and heated to 130° C. for 19 hours. After cooling, the volatiles were removed by Kugelrohr distillation at 0.1 mm and the residue was taken up in EtOAc/2 molar $NH_4OH$. The organic phase was washed with water, brine, dried ($Na_2SO_4$) and evaporated. The residue was chromatographed on a 50 mm×250 mm YMC-AQ RP HPLC column eluting with 70 percent acetonitrile (ACN) to give 61 mg (30 percent) of the purified off-white solid.

Preparation of 5-Bromo-N-[1-(4-methoxyphenyl)ethyl]thieno[2,3-d]pyrimidin-4-amine A mixture of 5-bromo-4-chlorothieno[2,3-d]pyrimidine (750 mg, 3.0 mmol), the amine hydrochloride (compound 117) (844 mg, 4.5 mmol) and triethylamine (606 mg, 6.0 mmol) in DMF (57 mL) was stirred at approximately 25° C. for 20 hours. After cooling, the mixture was diluted with water (20 mL) and extracted with ethyl acetate (3×25 mL). The combined organics were washed with water, saturated brine, and dried ($Na_2SO_4$). Filtration and removal of solvent gave crude material which was triturated with hexane, affording product as a tan solid, 840 mg, 2.3 mmol, 77 percent yield.

Example 50

5-Carboethoxy-N-[1-(4-methoxyphenyl)ethyl]thieno[2,3-d]pyrimidin-4-amine (Compound 50)

5-Bromo-N-[1-(4-methoxyphenyl)ethyl]thieno[2,3-d]pyrimidin-4-amine (200 mg, 0.55 mmol) was combined in 15 mL degassed, dry ethanol in a 45 mL pressure reactor with triethylamine (150 µl, 110 mg, 1.1 mmol, 2 eq.), palladium acetate (6 mg, 0.03 mmol, 5 mole percent) and 1,4-diphenylphosphinobutane (DPPB) (25 mg, 0.06 mmol, 10 mole percent). The reactor was purged, pressurized with carbon monoxide to 300 psi (21.1 $Kg/cm^2$) and heated at 120° C. for 18 hours. After cooling and release of pressure, the mixture was evaporated and the residue was taken up in EtOAc-water. The organic phase was washed with water, saturated brine, dried ($Na_2SO_4$) and evaporated. The crude material was purified by reverse phase HPLC chromatography on a 20 mm×250 mm YMC-AQ column eluting with 80 percent aqueous acetonitrile to yield 120 mg of product (61 percent) yield.

Example 51

5-Methoxy-4-[1-(4-methoxyphenyl)ethylamino]thieno[2,3-d]pyrimidine-6-carboxylic Acid Ethyl Ester (Compound 51)

A stirred solution of 4-chloro-5-methoxythieno[2,3-d]pyrimidine-6-carboxylic acid methyl ester (1.0 g, 3.8 mmol), 1-(4-methoxyphenyl)ethylamine (0.8 g, 5 mmol) and triethylamine (1 mL) in DMF (20 mL) was warmed to 60° C. for 1 hour. The reaction was diluted with water (50 mL) and extracted with ethyl acetate (2×50 mL). The combined organic phases were washed with brine, dried ($Na_2SO_4$), filtered and concentrated. The crude product was purified by chromatography over silica gel (25 percent EtOAc in hexanes) affording product as a powder (700 mg, 1.5 mmol).

Preparation of 4-chloro-5-methoxythieno[2,3-d]pyrimidine-6-carboxylic Acid Methyl Ester 4-Chloro-5-hydroxy-thieno[2,3-d]pyrimidine-6-carboxylic acid ethyl ester (0.4 g, 1.5 mmol) in tetrahydrofuran (10 mL) was slowly added to a slurry of sodium hydride (60 percent in mineral oil, 0.1 g 2.5 mmol) in tetrahydrofuran (30 mL) and stirred for one hour. Methyl iodide (2 mL) was added and the solution warmed to reflux for two hours. After cooling the reaction was quenched with water (100 mL) and extracted with ethyl acetate (2×100 mL). The combined organic extracts were washed with brine, dried ($NaSO_4$) and concentrated. The residue was purified by chromatography over silica (40 percent ethyl acetate/hexane) affording product as a yellow solid. (0.2 g, 50 percent) yield.

Example 52

5-Hydroxy-4-[1-(4-methoxyphenyl)ethylamino]thieno[2,3-d]pyrimidine-6-carboxylic Acid Ethyl Ester (Compound 52)

A stirred solution of 4-chloro-5-hydroxythieno[2,3-d]pyrimidine-6-carboxylic acid methyl ester (0.5 g, 1.9 mol), 1-(4-methoxyphenyl)ethylamine (0.4 g, 2.5 mol) and triethylamine (1 mL) in DMF (20 mL) was warmed to 60° C. for one hour. The reaction mixed was diluted with water (50 mL) and extracted with ethyl acetate (2×50 mL). The combined organic phases were washed with brine, dried ($Na_2SO_4$), filtered and concentrated. The residue was recrystallized from methylene chloride and hexane to give product (0.25 g, 0.7 mol, 36 percent) yield.

Preparation of 4-chloro-5-hydroxythieno[2,3-d]pyrimidine-6-carboxylic Acid Methyl Ester To a solution of 4,6-Dichloropyrimidine-5-carboxylic acid methyl ester (0.5 g, 2.5 mmol) (prepared as disclosed in Lee, C.-H., et. al. Bioorganic & Medicinal Chemistry Letters (2001), 11(18), 2419) and mercaptoacetic acid, ethyl ester (0.29 g 2.5 mmol) in acetonitrile (50 mL) was added triethylamine (2 mL) and the solution warmed to 50° C. for one hour. The reaction mixture was diluted with water (100 mL), made acidic (pH 2) with 2N HCl and the precipitate collected by filtration, giving product as a white solid, (0.6 g, 2.3 mmol, 92 percent) yield.

Examples 53-59

These examples were prepared by the process of Example 1 using the appropriate amines.

Example 60

This example was prepared according to Example 45 using the appropriate amine.

Examples 61-66

These examples were prepared by the process of Example 1 using the appropriate amines.

Example 67

This example was prepared according to Example 45 using the appropriate amine.

Examples 68-69

These examples were prepared by the process of Example 1 using the appropriate amines.

Example 70

(5-Iodothieno[2,3-d]pyrimidin-4-yl)-[1-(4-methoxyphenyl)ethyl]amine (Compound 70)

A mixture of 4-chloro-5-iodothieno[2,3-d]pyrimidine (100 mg, 0.34 mmol) and 1-(4-methoxyphenyl)ethylamine (69 mg, 0.37 mmol) and triethylamine (87 µL, 0.9 mmol) in DMF (2.0 mL) was allowed to react for 15 hours at 25° C., then 3 hours at 50° C. The reaction mixture was filtered through a cotton plug and purified by HPLC (Gilson system; Phenomenex column: Luna 5µ C18(2), 150×21.20 mm, 5µ micro) with water/acetonitrile gradient. Appropriate fractions were pooled to provide 70 mg of tan solid.

Preparation of 4-Chloro-5-iodothieno[2,3-d]pyrimidine

5-Bromo-4-chlorothieno[2,3-d]pyrimidine (1.0 g, 4.0 mmol) was partially dissolved in anhydrous THF (10 mL), cooled to 0° C. and treated over 1 minute with a 2.0 M THF solution of i-propylmagnesium chloride (3.0 mL, 6.0 mmol, 1.5 eq.). All solids went into solution. After stirring for 15 minutes, the mixture was treated dropwise with a solution of iodine (1.5 g, 6.0 mmol) in THF (8 mL), producing a copious precipitate. After 20 minutes, the reaction was quenched by addition of saturated aqueous $NH_4Cl$ and partitioned between ethyl acetate and water. The organic phase was washed with water, brine and dried ($Na_2SO_4$) to give 950 mg of the crude iodide-ca 90 percent pure by GC. This material was recrystallized from hot acetonitrile to give 840 mg (71 percent) of the purified iodide.

Example 71

This example was prepared as in Example 70 with the appropriate amine.

Examples 72-75

These examples were prepared by the process of Example 1 using the appropriate amines.

Example 76

(5-Fluorothieno[2,3-d]pyrimidin-4-yl)-[1-(4-methoxyphenyl)ethyl]amine (Compound 76)

A mixture of 4-chloro-5-fluorothieno[2,3-d]pyrimidine (50 mg, 0.27 mmol), the amine hydrochloride (compound 117) (65 mg, 0.35 mmol) and triethylamine (80 mg, 0.80 mmol) in DMF (0.5 mL) was stirred at approximately 25° C. for 40 hours. The solvent was evaporated and the residue purified by reverse phase chromatography on a YMC-AQ column (50 mm×250 mm) eluting with 70 percent acetonitrile. Product was isolated as a white solid, 54 mg, 0.18 mmol, 66 percent yield.

Preparation of 4-Chloro-5-fluorothieno[2,3-d]pyrimidine 5-bromo-4-chlorothieno[2,3-d]pyrimidine (3.0 g, 12 mmol) was dissolved in anhydrous THF (35 mL), cooled to 0° C. and treated in portions with a 2M THF solution of i-propylmagnesium chloride (6.8 mL, 13 mmol, 1.1 eq.). After 15 minutes the solution was treated in several portions with freshly distilled tributyltin chloride (5.0 mL, 5.9 g, 18 mmol, 1.5 eq.) and then allowed to warm to 25° C. and stir for 18 hours. The reaction was quenched by addition of saturated aqueous $NH_4Cl$ and worked up with EtOAc. The organic phase was washed with water, brine, dried ($Na_2SO_4$) and evaporated. The oily residue was stripped of volatiles by Kugelrohr distillation at 0.1 mm-pot temperature 80° C. The residue was subjected to chromatography on silica gel eluting with 3 percent EtOAc in hexanes to give the stannane-5.0 g (91 percent). This material was combined with F-TEDA (7.2 g, 20 mmol, 1.7 eq.) in acetonitrile (15 mL) and heated to 75° C. for 18 hours. After cooling, the mixture was diluted with 30 mL water and 50 mL EtOAc. The organic phase was separated and the aqueous phase was extracted with a further 50 mL EtOAc. The combined organic phases were stirred with 50 mL 10 percent aqueous $NH_4F$ solution for 1 hour. The precipitates were removed by filtration and the organic phase was washed with water, brine, dried ($Na_2SO_4$) and evaporated. The residue was Kugelrohr distilled at 0.1 mm and 4 g of a white solid was taken overhead. This material contained the desired 4-chloro-5-fluorothienopyrimidine, 4,5-dichloro and 4-chlorothienopyrimidine plus residual $Bu_3Sn$ components. This material was chromatographed on silica with 5 percent EtOAc/hexanes to give 790 mg of a white solid that was free of tributyltin residues. The 4-chloro-5-fluorothienopyrimidine was isolated by reverse phase-HPLC on a YMC-AQ column (50 mm×250 mm) by elution with 50 percent acetonitrile. Product was isolated as an off-white solid, 200 mg, 1.1 mmol, 8.9 percent yield.

Examples 77-78

These examples were prepared according to Example 76 with the appropriate amines.

Examples 79-83

These examples were prepared by the process of Example 1 using the appropriate amines.

Example 84

This example was prepared according to Example 76 with the appropriate amine.

Examples 85-87

These examples were prepared by the process of Example 1 using the appropriate amines.

Example 88

5-Methylthio-N-[1-(4-methoxyphenyl)ethyl]thieno[2,3-d]pyrimidin-4-amine (Compound 88)

A mixture of 4-chloro-5-methylthiothieno[2,3-d]pyrimidine (100 mg, 0.46 mmol), the amine hydrochloride (compound 117) (134 mg, 0.71 mmol) and triethylamine (196 mg, 1.9 mmol) in DMF (2 mL) was stirred at 50° C. for 3 hours. The solvent was evaporated and the residue purified by reverse phase chromatography on a YMC-AQ column (50 mm×250 mm) eluting with 75 percent acetonitrile. Product was isolated as a gold oil, 136 mg, 0.41 mmol, 89 percent yield.

Preparation of 4-Chloro-5-methylthiothieno[2,3-d]pyrimidine 5-bromo-4-chlorothieno[2,3-d]pyrimidine (750 mg, 3.0 mmol) was partially dissolved in anh. THF (8 mL), cooled to 0° C. and treated in portions with a 2M THF solution of i-PrMgCl (2.0 mL, 4.0 mmol). After 20 minutes, this solution was treated dropwise with methylmethanethiosulfonate (460 µl, 570 mg, 4.5 mmol). The cooling bath was removed and the mixture was stirred for 4 hours at 25° C. The reaction was quenched with saturated aqueous $NH_4Cl$ and extracted with EtOAc. The organic phase was washed with water, brine, dried ($Na_2SO_4$) and evaporated to give 830 mg crude product-ca 80 percent pure by GC. The material was purified by recrystallization from hot heptane to give 350 mg (45 percent) yield of tan crystals.

Example 89

5-Methanesulfonyl-N-[1-(4-methoxyphenyl)ethyl]thieno[2,3-d]pyrimidin-4-amine (Compound 89)

A mixture of 4-chloro-5-methanesulfonylthieno[2,3-d]pyrimidine (100 mg, 0.40 mmol), the amine hydrochloride (compound 117) (113 mg, 0.60 mmol) and triethylamine (150 mg, 1.5 mmol) in DMF (1.5 mL) was stirred at approximately 25° C. for 19 hours. The solvent was evaporated and the residue purified by reverse phase chromatography) on a YMC-AQ column (50 mm×250 mm) eluting with 75 percent acetonitrile. Product isolated as a gold oil, 122 mg, 84 percent.

Preparation of 4-Chloro-5-methanesulfonylthieno[2,3-d]pyrimidine

4-Chloro-5-methylthiothieno[2,3-d]pyrimidine (150 mg, 0.69 mmol) was dissolved in dichloromethane (6 mL), cooled to −5° C. and treated with 70 percent m-chloroperbenzoic acid (512 mg, ca 2.1 mmol, 3 eq.). The cooling bath was removed and the mixture was stirred at 25° C. for 4 hours. The mixture was stirred with excess dilute $NaHSO_3$ solution and the separated organic phase was washed with saturated $NaHCO_3$, water, brine, dried ($Na_2SO_4$) and evaporated to give 150 mg (87 percent) yield of material that was used without further purification.

Examples 90-93

These examples were prepared by the process of Example 1 using the appropriate amines.

Examples 1a-10a

These examples were prepared by the process of Example 1 using the appropriate amines.
TABLE 2 lists the compounds of Examples 1-93.
TABLE 3 lists the compounds of Examples 1a-10a.

TABLE 2

| Compound No. | Structure | Mass Spec Characterization | m.p. | Compound No. | Structure | Mass Spec Characterization | m.p. |
|---|---|---|---|---|---|---|---|
| 1 | 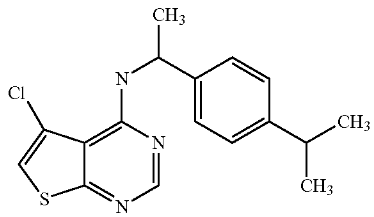 | | 71-2 | 17 | 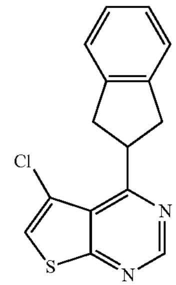 | 288 (M + H) | |
| 2 | 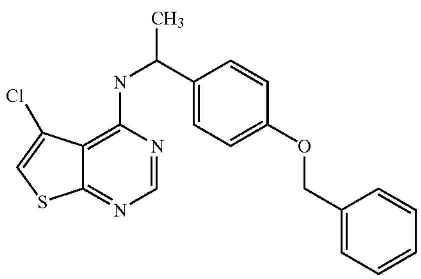 | | 85 | 18 | 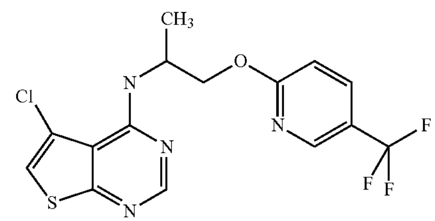 | 389 (M + H) | |
| 3 | 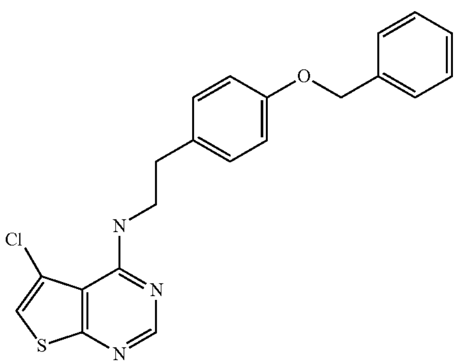 | | 92-3 | 19 | 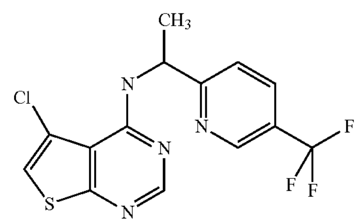 | 359 (M + H) | |

TABLE 2-continued

| Compound No. | Structure | Mass Spec Characterization | m.p. | Compound No. | Structure | Mass Spec Characterization | m.p. |
|---|---|---|---|---|---|---|---|
| 4 | 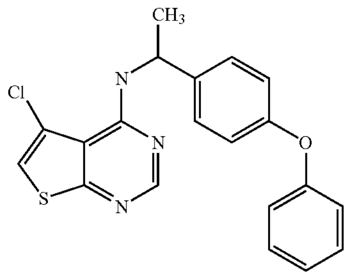 | 380 (M + H) | | 20 | 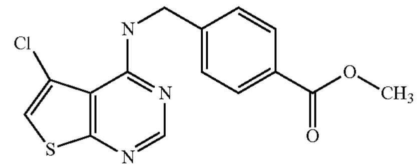 | 336 (M + H) | |
| 5 | 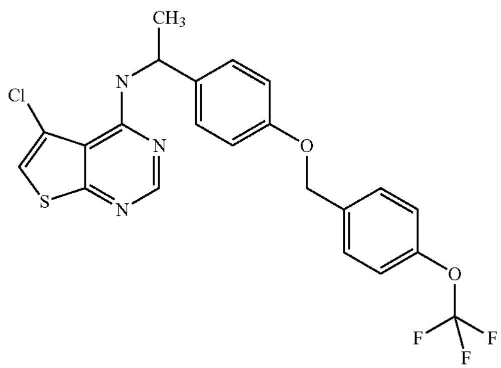 | 480 (M + H) | | 21 | 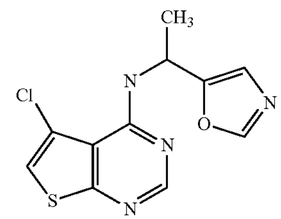 | 381 (M + H) | |
| 6 | 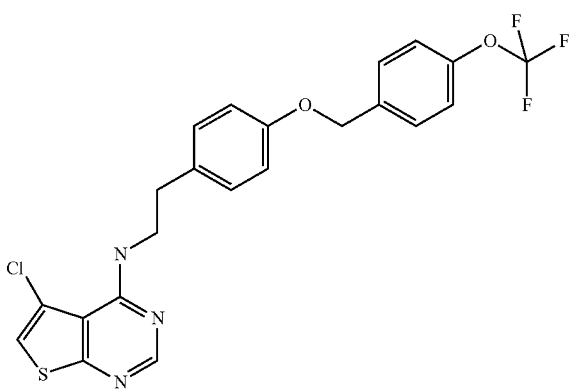 | 480 (M + H) | | 22 | 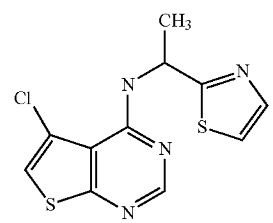 | 397 (M + H) | |

TABLE 2-continued

| Compound No. | Structure | Mass Spec Characterization | m.p. | Compound No. | Structure | Mass Spec Characterization | m.p. |
|---|---|---|---|---|---|---|---|
| 7 | 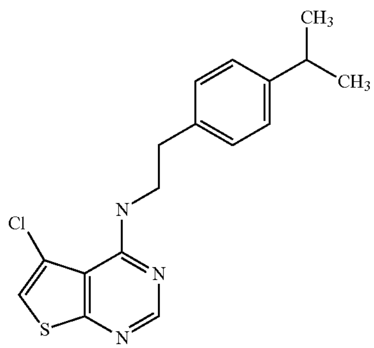 | 332 (M + H) | | 23 | 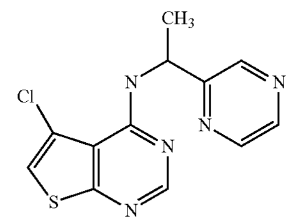 | 292 (M + H) | |
| 8 | 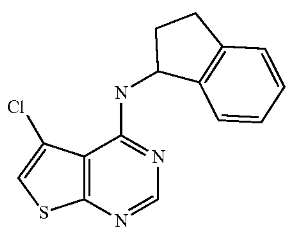 | 302 (M + H) | | 24 | 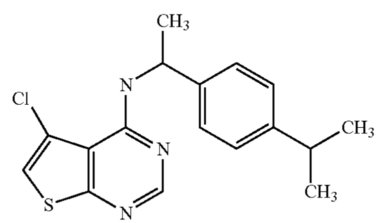 | 332 (M + H) | |
| 9 | 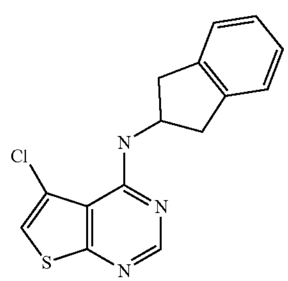 | 302 (M + H) | | 25 | 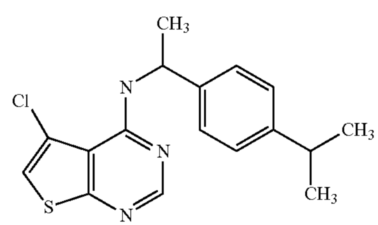 | 332 (M + H) | |

TABLE 2-continued

| Compound No. | Structure | Mass Spec Characterization | m.p. | Compound No. | Structure | Mass Spec Characterization | m.p. |
|---|---|---|---|---|---|---|---|
| 10 | 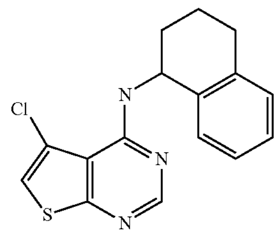 | 316 (M + H) | | 26 | 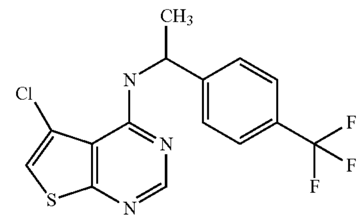 | 358 (M + H) | |
| 11 | 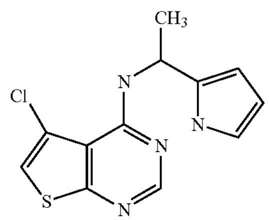 | 279 (M + H) | | 27 | 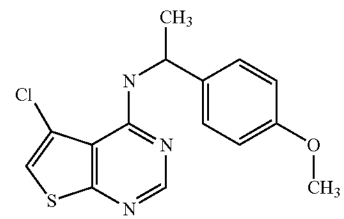 | 320 (M + H) | |
| 12 | 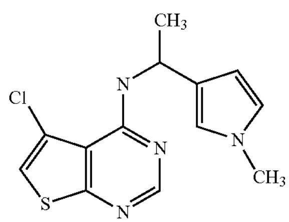 | 293 (M + H) | | 28 | 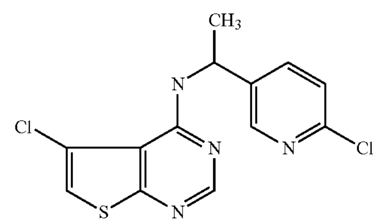 | 325 (M + H) | |
| 13 | 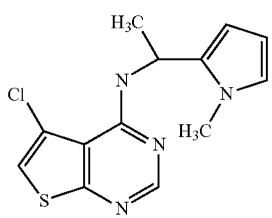 | 293 (M + H) | | 29 | 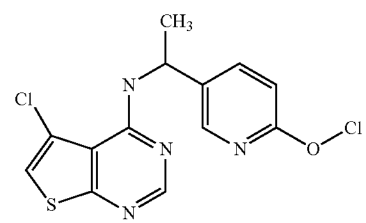 | 321 (M + H) | |

TABLE 2-continued

| Compound No. | Structure | Mass Spec Characterization | m.p. | Compound No. | Structure | Mass Spec Characterization | m.p. |
|---|---|---|---|---|---|---|---|
| 14 | 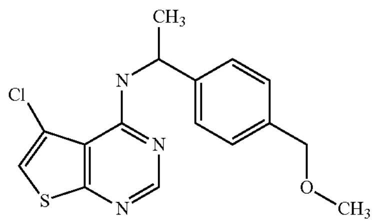 | 334 (M + H) | | 30 | 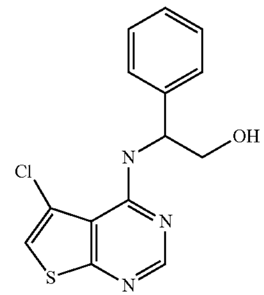 | | 120 |
| 15 | 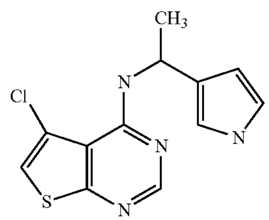 | 279 (M + H) | | 31 | 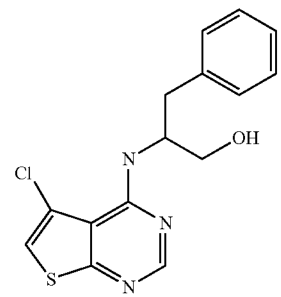 | | 104-5 |
| 16 | 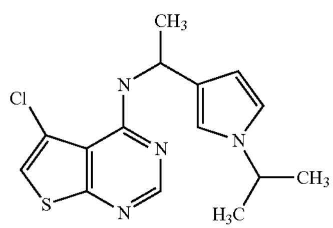 | 321 (M + H) | | 32 | 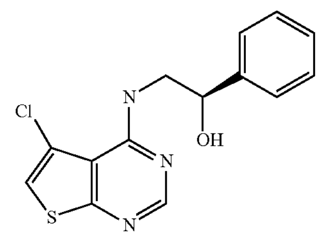 | | 111-2 |

TABLE 2-continued

| Compound No. | Structure | Mass Spec Characterization | m.p. |
|---|---|---|---|
| 33 | (benzyl-CH(CH2OH)-CH2- attached to 7-chlorothieno[3,2-d]pyrimidin-4-yl) | | 176-7 |
| 34 | 4-[1-(pyridin-2-yl, 5-(1-methylethyl))ethylamino]-7-chlorothieno[3,2-d]pyrimidine | 333 (M + H) | |
| 35 | 4-[1-(5-benzyloxypyridin-2-yl)ethylamino]-7-chlorothieno[3,2-d]pyrimidine | 397 (M + H) | |
| 36 | 4-[1-(5-methoxypyridin-2-yl)ethylamino]-7-chlorothieno[3,2-d]pyrimidine | 322 (M + H) | |
| 49 | 4-[1-(4-methoxyphenyl)ethylamino]-6-cyanothieno[3,2-d]pyrimidine | 311 (M + H) | |
| 50 | ethyl 4-[1-(4-methoxyphenyl)ethylamino]thieno[3,2-d]pyrimidine-6-carboxylate | 357 (M) | |
| 51 | ethyl 4-[1-(4-methoxyphenyl)ethylamino]-7-methoxythieno[3,2-d]pyrimidine-6-carboxylate | 388 (M + H) | |
| 52 | ethyl 4-[1-(4-methoxyphenyl)ethylamino]-7-hydroxythieno[3,2-d]pyrimidine-6-carboxylate | | 151-2 |

TABLE 2-continued

| Compound No. | Structure | Mass Spec Characterization | m.p. | Compound No. | Structure | Mass Spec Characterization | m.p. |
|---|---|---|---|---|---|---|---|
| 37 | 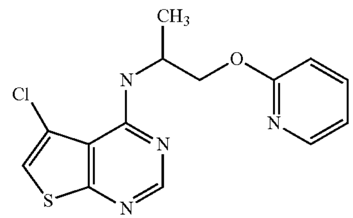 | 321 (M + H) | | 53 | 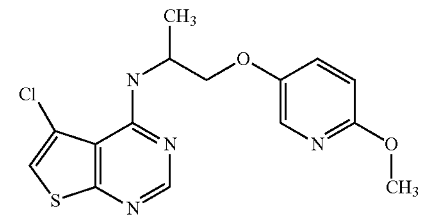 | 351 (M + H) | |
| 38 | 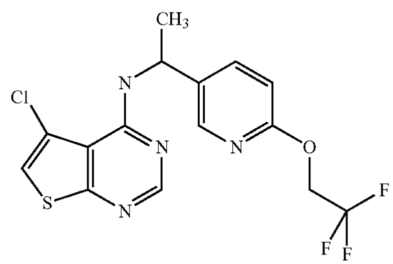 | 389 (M + H) | | 54 | 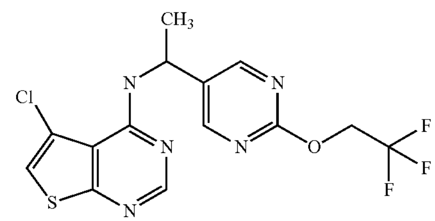 | 390 (M + H) | |
| 39 | 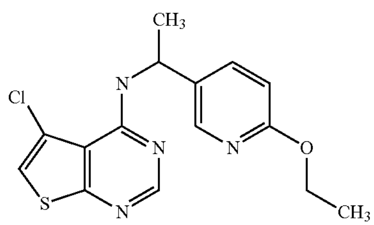 | 335 (M + H) | | 55 | 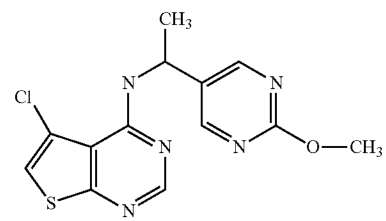 | 322 (M + H) | |
| 40 | 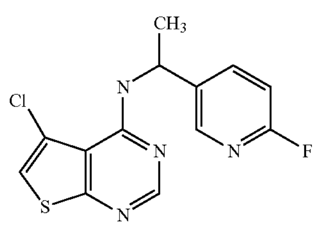 | 309 (M) | | 56 | 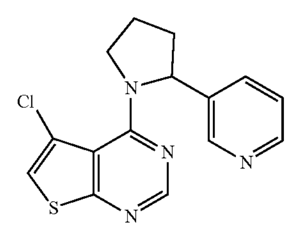 | 317 (M + H) | |

TABLE 2-continued

| Compound No. | Structure | Mass Spec Characterization | m.p. | Compound No. | Structure | Mass Spec Characterization | m.p. |
|---|---|---|---|---|---|---|---|
| 41 | 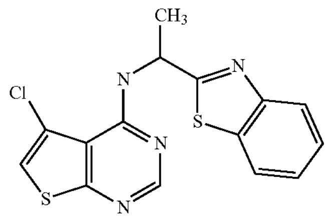 | 347 (M + H) | | 57 | 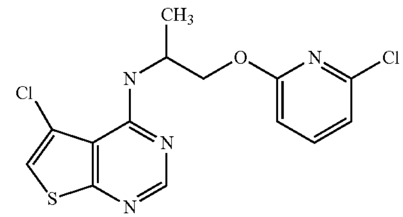 | 355 (M + H) | |
| 42 | 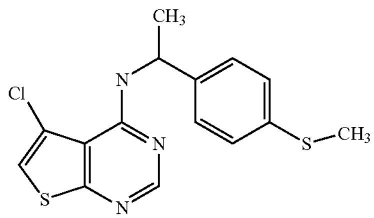 | 336 (M + H) | | 58 | 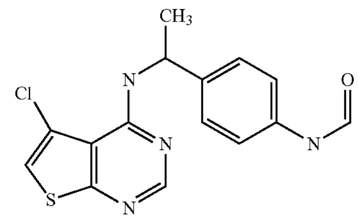 | 331 (M − H) | |
| 43 | 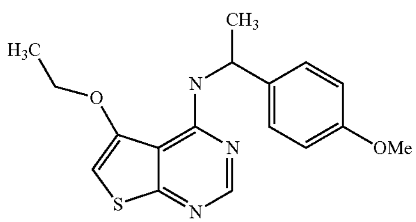 | 329 (M + H) | | 59 | 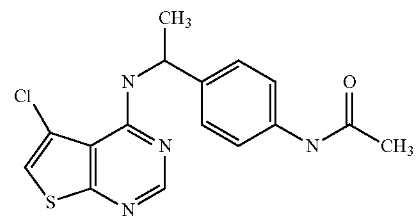 | 347 (M + H) | |
| 44 | 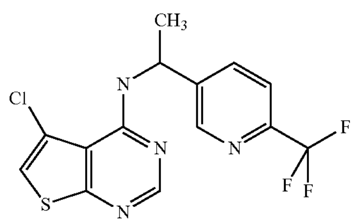 | 358 (M) | | 60 | 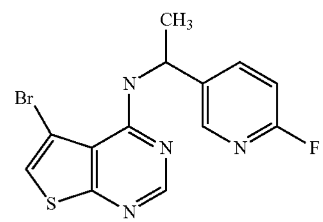 | 353 (M + 1) | |

TABLE 2-continued
| Compound No. | Structure | Mass Spec Characterization | m.p. | Compound No. | Structure | Mass Spec Characterization | m.p. |
|---|---|---|---|---|---|---|---|
| 45 | 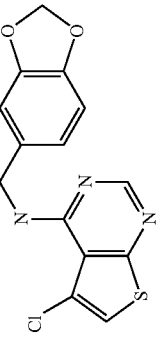 | 364 (M) | | 61 | 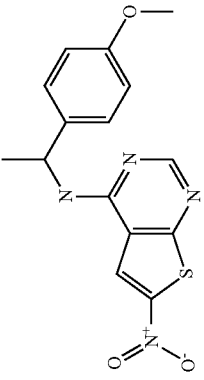 | 334 (M + H) | |
| 46 | 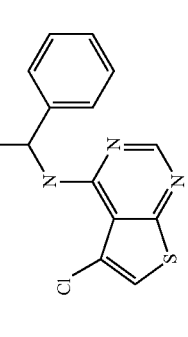 | 330 (M) | | 62 | 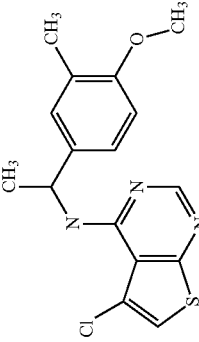 | 320 (M + H) | |
| 47 | 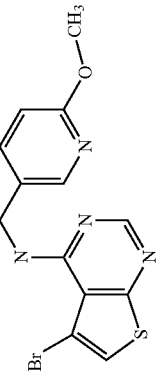 | 331 (M + H) | | 63 | 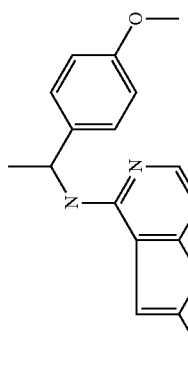 | 334 (M + H) | |
| 48 | 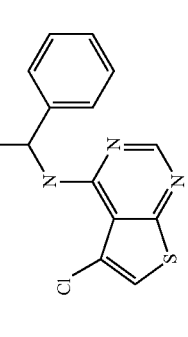 | 363 (M) | | 64 | 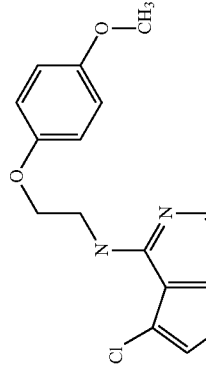 | 336 (M + H) | |

TABLE 2-continued

| Compound No. | Structure | Mass Spec Characterization | m.p. | Compound No. | Structure | Mass Spec Characterization | m.p. |
|---|---|---|---|---|---|---|---|
| 65 | 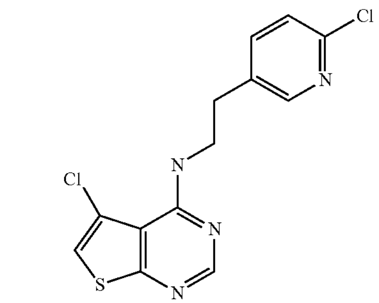 | 325 (M + H) | | 80 | 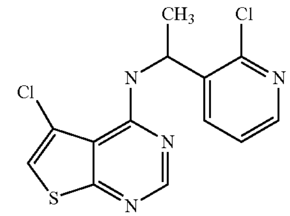 | 324 (M + H) | |
| 66 | 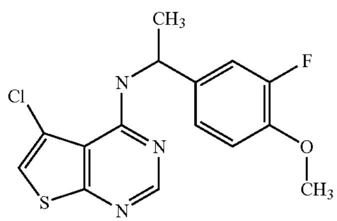 | 338 (M + H) | | 81 | 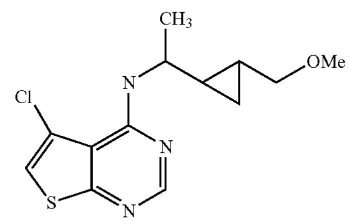 | 298 (M + H) | |
| 67 | 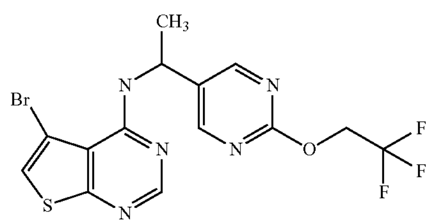 | 434 (M + H) | | 82 | 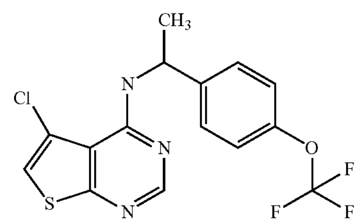 | 374 (M + H) | |
| 68 | 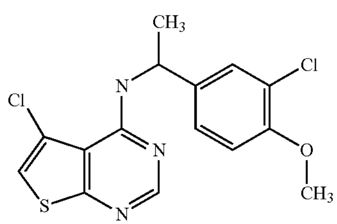 | 384 (M) | | 83 | 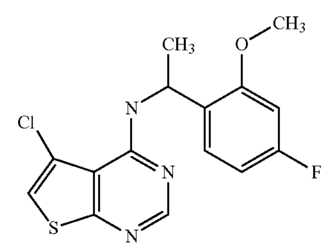 | (M + H) | |

TABLE 2-continued

| Compound No. | Structure | Mass Spec Characterization | m.p. |
|---|---|---|---|
| 69 | (structure) | 306 (M + H) | |
| 70 | (structure) | 412 (M + H) | |
| 71 | (structure) | 413 (M + H) | |
| 72 | (structure) | 327 (M + H) | |
| 84 | (structure) | 372 (M) | |
| 85 | (structure) | 404 (M + H) | |
| 86 | (structure) | 390 (M + H) | |
| 87 | (structure) | 365 (M) | |

TABLE 2-continued

| Compound No. | Structure | Mass Spec Characterization | m.p. |
|---|---|---|---|
| 73 | | 388 (M + H) | |
| 74 | | 371 (M + H) | |
| 75 | | 353 (M + H) | |
| 88 | | 331 (M) | |
| 89 | | 363 (M) | |
| 90 | | 395 (M + H) | |

TABLE 2-continued

| Compound No. | Structure | Mass Spec Characterization | m.p. |
|---|---|---|---|
| 76 | | 303 (M) | |
| 77 | | 304 (M) | |
| 78 | | 371 (M) | |
| 79 | | 335 (M + H) | |
| 91 | | 346 (M + H) | |
| 92 | | 332 (M + H) | |
| 93 | | 330 (M + H) | |

TABLE 3
| Compound No. | Structure | Mass Spec Characterization |
|---|---|---|
| 1a | 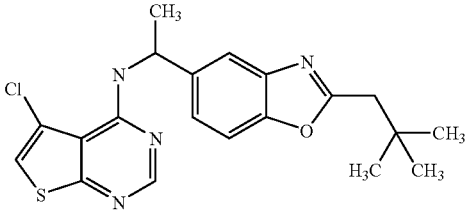 | 400 (M + H) |
| 2a | 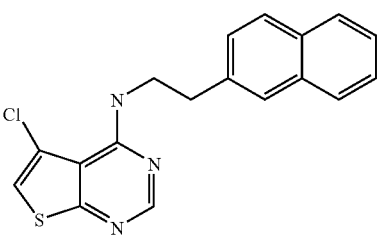 | 340 (M + H) |
| 3a | 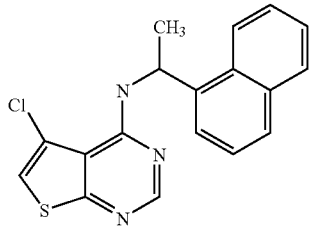 | 340 (M + H) |
| 4a | 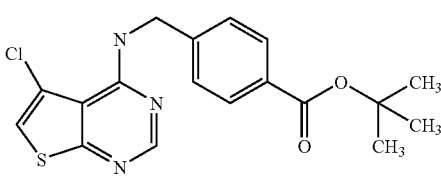 | 376 (M + H) |
| 5a | 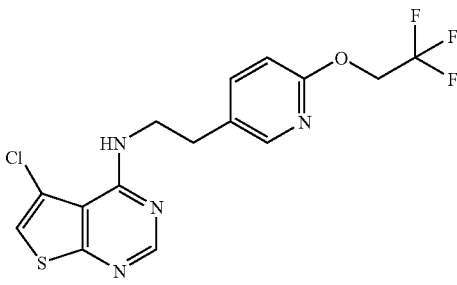 | 388 (M + H) |
| 6a | 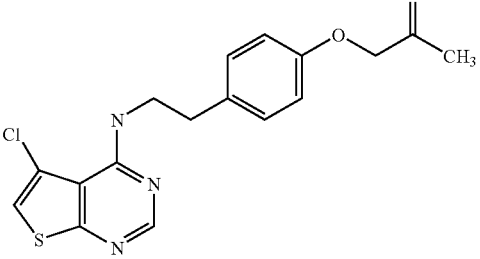 | 362 (M + H) |

TABLE 3-continued

| Compound No. | Structure | Mass Spec Characterization |
|---|---|---|
| 7a | 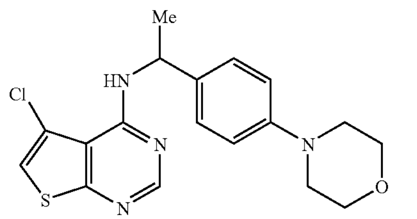 | 375 (M + H) |
| 8a | 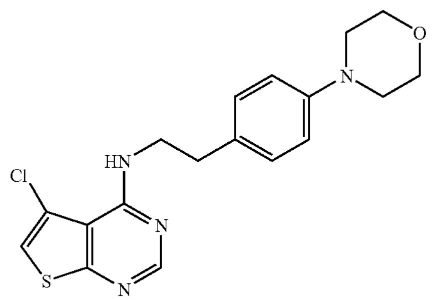 | 375 (M + H) |
| 9a | 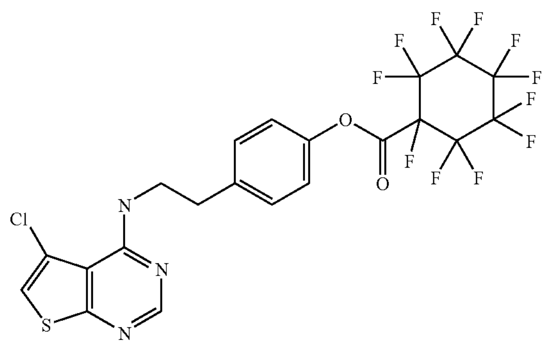 | 613 (M + H) |
| 10a | 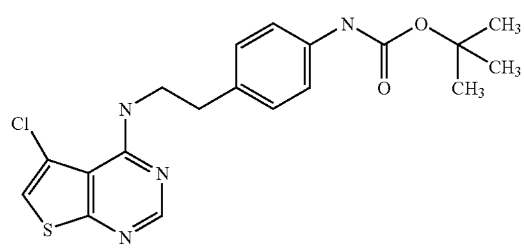 | 370 (M + H) |

Preparation of Intermediates and Starting Materials

Preparation of 2-[(5-chlorothieno[2,3-d]pyrimidinyl-4)amino]-1-propanol (Compound 94)

2-Amino-1-propanol (0.44 g, 5.8 mmol) was added to a solution of 4,5-dichlorothieno[2,3-d]pyrimidine (prepared as disclosed in EP 447891) (1.0 g, 4.9 mmol) and Et$_3$N (0.8 mL) in DMF (20 mL). The mixture was stirred for 3 hours, diluted with H$_2$O (25 mL) and extracted with Et$_2$O (3×50 mL). The organics portions were combined, washed with brine, dried with Na$_2$SO$_4$, and filtered. Solvent was removed in vacuo yielding a light yellow solid. This solid was washed with 3-4 mL of a 10 percent Et$_2$O/pentane solution and solid was filtered off giving product as a light tan solid, 880 mg.

Preparation of 1-Isoxazol-5-yl-ethanamine (Compound 109)

This compound was prepared according to: Ohba, Masashi; Kubo, Hiroyuki; Fujii, Tozo; Ishibashi, Hiroyuki; Sargent, Melvyn V.; Arbain, Dayar. *Tetrahedron Lett.* 1997, 38, 6697.

Preparation of 2-(1-Aminoethyl)pyrazine (Compound 111)

This compound was prepared from compound 167 according to: Thompson, Wayne J.; Sugrue, Michael F.; Ransom, Richard W.; Mallorga, Pierre J.; Bell, Ian M.; Smith, Anthony M. WO 9613262 A1.

Preparation of 1-(6-Chloropyridin-2-yloxy)-2-propylamine (Compound 130)

Sodium hydride (60 wt. percent oil dispersion, 560 mg, 14 mmol) was added to a stirred solution of 2-aminopropanol (1.2 mL, 14 mmol) in THF (25 mL). After 30 minutes, 2,6-dichloropyridine (2.0 g, 14 mmol) was added and the reaction heated at reflux for 8 hours. After cooling, the reaction was quenched with aqueous 1N hydrochloric acid and washed with ether (3×30 mL). The pH of the aqueous phase was then raised to 10-11 with 50 wt. percent aqueous sodium hydroxide and extracted with ether (3×50 mL). The organics were dried ($MgSO_4$), filtered and solvent removed in vacuo leaving 2.2 g of a yellow oil.

Preparation of 1-[4-(4-Trifluoromethoxybenzyloxy)phenyl]ethanone (Compound 156)

A stirred mixture of 4-hydroxyacetophenone (0.9 g, 6.6 mmol), 4-(trifluoromethoxy)benzyl bromide (2.0 g, 7.8 mmol) and potassium carbonate (1.4 g, 10 mmol) in acetone (25 mL) was heated at reflux for 7 hours. The mixture was then cooled, diluted with $H_2O$ (50 mL) and extracted with EtOAc (2×100 mL). The organic portions were combined, washed with brine and dried ($Na_2SO_4$). Filtration and removal of solvent in vacuo afforded 2.1 g of a crude yellow semi-solid which was used without further purification.

Preparation of [4-(4-Trifluoromethoxybenzyloxy)phenyl]acetonitrile (Compound 157)

A mixture of 4-(trifluoromethoxy)benzyl bromide (2.5 g, 10 mmol), 4-hydroxybenzyl cyanide (1.1 g, 8 mmol) and potassium carbonate (1.4 g, 10 mmol) in acetone (25 mL) was heated to reflux for 7 hours. The mixture was then diluted with $H_2O$ (100 mL) and extracted with EtOAc (2×150 mL). Organics portions were combined and washed with brine and then dried with $Na_2SO_4$. The mixture was then filtered and the solvent was removed in vacuo affording 2.5 g of crude product. Purification by flash chromatography eluting with 30 percent ether/pentane over silica gel yielded 2.2 g of a white solid.

Preparation of 1-(1-isopropyl-1H-pyrrol-3-yl)ethanone (Compound 164)

Potassium t-butoxide (6.7 g, 60 mmol) was added to a stirred 0° C. solution of 1-(1H-pyrrol-3-yl)ethanone (5.0 g, 46 mmol) of DMF (150 mL). After stirring for 30 minutes, 2-iodopropane (10.1 g, 60 mmol) was added and the mixture was stirred overnight at approximately 25° C. The mixture was diluted with $Et_2O$ and $H_2O$. The portions were separated, and the aqueous portion was extracted two more times. The organic portions were combined and washed with brine and then dried with $Na_2SO_4$. The mixture was filtered and the solvent removed in vacuo. The crude product was purified by flash chromatography (30 percent ether/pentane over silica gel), affording 3.9 g of yellow oil.

Preparation of 1-(5-Methoxypyridin-2-yl)ethanone (Compound 169)

A 3M THF solution of methyl magnesium bromide (2.6 mL) was added to a chilled (−78° C.) stirred solution of compound 208 (1.4 g, 7.1 mmol) in THF (25 mL). After addition the temperature was allowed to rise to −40° C. The mixture was stirred for two hours, and then quenched with a saturated $NH_4Cl$ solution. The resulting mixture was extracted three times with $Et_2O$. The organic portions were combined, washed with $H_2O$, saturated brine and then dried ($Na_2SO_4$). The mixture was filtered and concentrated in vacuo. The residue was purified via flash chromatography (30 percent ether/pentane over silica gel), yielding a white solid, 880 mg, 5.8 mmol, 82 percent yield.

The following compound was prepared using compound 209 according to the procedure above for compound 169: 1-(5-Benzyloxypyridin-2-yl)ethanone (compound 173)

Preparation of 5-Methoxypyridine-2-carboxylic Acid, N-methoxy-N-methyl Amide (Compound 208)

A 2M hexanes solution of $Me_3Al$ (2.4 mL) was slowly added to a cooled (0° C.) solution of N,O-dimethylhydroxylamine HCl (438 mg, 4.5 mmol) in dry THF (5 mL). After complete addition and gas evolution ceased, the reaction was warmed to approximately 25° C. over 30 minutes. This solution was then slowly added to a cooled (0° C.) solution of compound 206 (500 mg, 3.0 mmol) in THF (3 mL). This mixture was stirred for 5 minutes and then allowed to warm to approximately 25° C. over 3 hours. The mixture was then cooled to 0° C. and quenched with careful addition of brine. The pH was adjusted to 11 by addition of solid $Na_2CO_3$, and the resulting mixture was filtered through Celite™. The filtrate was extracted 3 times with $CH_2Cl_2$ and the organics portions were combined, dried ($Na_2SO_4$) and filtered. Solvent was stripped in vacuo, and the residue purified via chromatography (20 vol percent $CH_3CN$ in $CH_2Cl_2$ over silica gel) yielding a yellow oil, 434 mg, 2.2 mmol, 74 percent yield.

The following compound was prepared using compound 207 according to the procedure used in preparing Compound 208: 5-Benzyloxypyridine-2-carboxylic acid, N-methoxy-N-methyl amide (compound 209)

Preparation of Methyl 5-methoxypyridine-2-carboxylate (Compound 206)

A solution of compound 205 (4 g) in DMF (5 mL) was added dropwise to a stirred suspension of sodium hydride dispersion (4 g, 0.1 mol) in DMF (90 mL). After 30 min. iodomethane (4.1 g) was added. After 30 minutes of stirring an additional 1 g of NaH was added, and stirring continued for another 30 minutes. The mixture was quenched by careful addition of saturated brine solution and extracted three times with $CH_2Cl_2$. The organic portions were combined, dried ($Na_2SO_4$), and filtered. Removal of solvent in vacuo left a residue that was purified by flash chromatography (40 percent ether/pentane over silica gel), yielding 1.9 g of yellow solid.

The following compound was prepared using benzyl bromide according to the procedure above for compound 206: Methyl 5-benzyloxypyridine-2-carboxylate (compound 207)

Preparation of Methyl 5-hydroxypyridine-2-carboxylate (Compound 205)

To 5-hydroxypyridine-2-carboxylic acid (5.0 g, 36 mmol) suspended in $CH_2Cl_2$ (120 mL) was added DMF (1 mL) followed by oxalyl chloride (4.7 g, 37 mmol). After 1 hour, excess MeOH was added. The resulting mixture was stripped of solvent in vacuo yielding a brown solid that was washed with hot EtOAc. Yielded 4.6 g of product.

Preparation of 1-(5-Methoxypyrimidin-2-yl)ethanone (Compound 174)

To a solution of 2-cyano-5-methoxypyrimidine (4.73 g, 0.035 mol) in benzene (100 mL) was added 3.0 M methyl magnesium iodide in ether (15 mL) at 0° C. under stirring. Once the addition was over, the reaction was stirred at approximately 25° C. for 2 hours. The reaction was quenched with saturated aqueous $NH_4Cl$ solution at 0° C. To the mixture was added 2N HCl (20 mL) solution and brine. After separation of the two phases, the aqueous phase was extracted with $CH_2Cl_2$ three times. The combined organic layer was dried over $Na_2SO_4$, filtered, concentrated and purified on silica gel using 5 percent MeOH in $CH_2Cl_2$ to give 3.0 g a yellowish solid in 56 percent yield.

Preparation of 1-(6-Ethoxypyridin-3-yl)ethanone (Compound 176)

A 2.5 M solution of butyllithium in hexanes (4.67 mmol) was added dropwise to a −78° C. solution of compound 210 (0.90 g, 4.4 mmol) in THF (9 mL) and then stirred for 90 minutes. N-Methoxy-N-methylacetamide (0.92 g, 8.9 mmol) was then added dropwise to this mixture and stirred for 90 min. Upon completion of reaction, the mixture was warmed to approximately 25° C., diluted with $NaHCO_3$ (aqueous) and extracted with $Et_2O$. The organics were combined, dried over anhydrous $MgSO_4$, and concentrated in vacuo, leaving 735 mg of a dark yellow oil, which was used without further purification.

Preparation of 5-Bromo-2-ethoxypyridine (Compound 210)

This was prepared according to Butora, G., et. al. *J. Am Chem. Soc.* 1997, 119, 7694, substituting NaOEt and ethanol for NaOMe and methanol.

Preparation of 1-(6-Trifluoromethylpyridin-3-yl)ethanone (Compound 180)

A 3 M solution of MeMgBr in $Et_2O$ (7.2 mmol) was added to a stirred solution of 6-(trifluoromethyl)nicotinonitrile (0.82 g, 4.8 mmol) in ether (16 mL) dropwise over a 30 minute period. The reaction was stirred for 2 hours then the mixture was quenched with aqueous 1N HCl and extracted with $Et_2O$. The organics were combined and washed with brine and dried over anhydrous $MgSO_4$. The solvent was removed in vacuo yielding 530 mg of a brown solid.

Preparation of 1-[(6-methoxypyridin-3-yl)oxy]acetone (Compound 181)

A solution of chloroacetone (3.7 g) and potassium iodide (65 mg) in acetone (7 mL) was stirred at approximately 25° C. overnight. In a second reactor, 6-methoxypyridin-3-ol (4.0 g, mmol) and potassium carbonate (1.3 g, 10 mmol) in acetone (5 mL) was refluxed for 15 min., then ¼ of chloroacetone/KI solution was added followed by additional potassium carbonate (1.3 g). This was repeated three times more, then the reaction stirred at approximately 25° C. overnight. The mixture was concentrated in vacuo. The residue was dissolved in $Et_2O$ and washed with $H_2O$, brine and dried with $Na_2SO_4$. The solution was filtered and concentrated in vacuo yielding 3.5 g of clear oil that was used without further purification. This material darkened on standing over time.

Preparation of 6-Methoxypyridin-3-ol

A 2.5 M hexane solution of n-butyllithium (23 mL, 58 mmol) was added over 30 minutes to a −78° C. solution of 5-bromo-2-methoxypyridine (10 g, 53 mmol) in ether (120 mL), keeping the temperature below −65° C. The slurry was stirred for 30 minutes, and then trimethylborate (6.1 mL) was added quickly to the reaction solution. Again the temperature was maintained below −65° C. The solution was stirred for 10 minutes, warmed to 15° C. and then cooled to −78° C. Peracetic acid (56 mmol) was added dropwise, while the temperature was kept at or below −65° C. After addition, the reaction was warmed briefly to −50° C., cooled back to −65° C., then stirred at approximately 25° C. overnight. The reaction was quenched with water (100 mL), and then extracted with ether (3×150 mL). The organic portions were combined and washed with aqueous $NaHSO_3$ solution and brine. The organic portions were extracted two times with 2N aqueous NaOH solution. The pooled basic aqueous fractions were washed with $Et_2O$ and then acidified with $NaHSO_4$. The product precipitated out as oil; the aqueous mixture was extracted three times with $Et_2O$, the pooled ether fractions were dried with $Na_2SO_4$, and stripped of solvent in vacuo. Yielded 3.6 g of a brown solid.

Preparation of 5-Acetyl-2-(trifluoroethoxy)pyrimidine (Compound 182)

Dichlorobis(triphenylphosphine)palladium (II) (215 mg, 0.3 mmol) was added to a solution of the bromopyrimidine (compound 211) (7.7 g, 30 mmol) and tributyl(1-ethoxyvinyl)tin (11.9 g, 33 mmol) in anhydrous toluene (100 mL), and the mixture stirred at 100° C. for 4 hours. The reaction was cooled to 5° C. and 2M HCl (50 mL) was added. The reaction was allowed to warm to approximately 25° C., and after 2 hours, filtered through Celite™. The layers were separated, and the organic layer rapidly stirred with a solution of potassium fluoride (9 g, 0.15 mol) in water (50 mL) for 30 minutes. Both layers were filtered through Celite™, the layers separated, and the organic layer washed with brine, dried ($Na_2SO_4$), filtered and stripped. The crude brown solid residue was "vacuum" chromatographed on silica using 1 vol. percent $CH_3CN$ in $CH_2Cl_2$ giving a white solid, 3.8 g, 57 percent yield.

The following compound was prepared using compound 212 according to the procedure for Compound 182: 1-(2-Methoxypyrimidin-5-yl)ethanone (compound 183)

Preparation of 5-Bromo-2-(trifluoroethoxy)pyrimidine (Compound 211)

A mechanically stirred slurry of 5-bromo-2-(methanesulfonyl)pyrimidine (24 g, 0.10 mol), trifluoroethanol (15 g, 0.15 mol), and potassium carbonate (28 g, 0.20 mol) in acetonitrile (250 mL) was heated at 70° C. for 12 hours. HPLC analysis indicated complete conversion. The solids were removed by filtration, and rinsed well with acetonitrile. The solvent was removed in vacuo and the residue partitioned between ether (50 mL) and water (25 mL). The aqueous phase was extracted with ether (2×25 mL), the organic layers combined, and washed with brine. Dried (Na$_2$SO$_4$), filtered, and solvent removed in vacuo, affording product as a pale yellow liquid, 19 g, 74 percent yield.

The following compound was prepared according to the procedure for Compound 182:

5-Bromo-2-(methoxy)pyrimidine (compound 212)

Preparation of 4-Formamidoacetophenone (Compound 184)

A solution of 98 percent formic acid (15.3 mL, 0.4 mol) and acetic anhydride (41 g, 0.4 mmol) was stirred at 0-5° C. for 1 hour. The resulting formic anhydride was added to 4-aminoacetophenone and the mixture was stirred at approximately 25° C. overnight and then poured into water and neutralized with saturated aqueous Na$_2$CO$_3$ at approximately 25° C. The mixture was then extracted with CH$_2$Cl$_2$ 3 times. The combined organic layer was dried over Na$_2$SO$_4$, filtered, concentrated to give 4.6 g product in 95 percent yield.

Preparation of 4-Methoxy-3-methylacetophenone (Compound 188)

To a suspension of sodium hydride (60 percent in mineral oil, 1.44 g, 36 mmol) in anhydrous DMF (30 mL) was added dropwise a solution of 4-hydroxy-3-methylacetophenone (4.5 g, 30 mmol) in dry DMF (20 mL) at 0° C. over a period of 20 minutes. After addition, the mixture was stirred at 0° C. for 30 minutes and iodomethane (2.2 mL, 36 mmol) was added in one portion. The mixture was then stirred at approximately 25° C. overnight. Water was added (10 mL) and the mixture was extracted with ether three times. The combined organic layer was washed with brine, dried over Na$_2$SO$_4$, filtered, concentrated, and dried under vacuum to give crude product as a colorless oil.

Preparation of 1-(2-Methoxy-1,3-thiazol-5-yl)ethanone (Compound 192)

Sodium methoxide (25 wt percent in methanol, 2.7 mL) was added to a solution of compound 213 in MeOH (15 mL) and the solution stirred at approximately 25° C. for 2 hours. The reaction was quenched by the addition of aqueous 1M hydrochloric acid until pH was neutral. The solvents were removed in vacuo, the residue dissolved in Et$_2$O and washed with water, and brine. The organics were then dried with Na$_2$SO$_4$ and filtered through silica gel. The solvent was removed in vacuo yielding 0.84 g of an off-white powder.

The following compound was prepared using trifluoroethanol according to the procedure used in preparing compound 192: 1-[2-(2,2,2-trifluoroethoxy)-1,3-thiazol-5-yl]ethanone (compound 204)

Preparation of 1-(2-chloro-1,3-thiazol-5-yl)ethanone (Compound 213)

A solution of 2-chlorothiazole (5.0 g, 42 mmol) in THF (10 mL) was added dropwise to a −78° C. solution of n-BuLi (2.5 M in hexanes; 18.4 mL, 46 mmol) in THF (140 mL). The solution was stirred for 1 hour, and then N-methoxy-N-methylacetamide (4.7 g, 46 mmol) was added. The mixture was stirred for another hour, and then it was warmed to approximately 25° C. The reaction was quenched by the addition of a saturated aqueous ammonium chloride solution and extracted with ether (3×75 mL). The organics were combined, washed with brine, filtered and then concentrated. The residue was purified by flash chromatography (20 percent ether/pentane on silica gel), yielding 5.9 grams of yellow semi-solid.

Preparation of 1-(6-Methoxy-pyridin-3-yl)-propan-1-one (Compound 196)

Sodium methoxide (2.8 g, 50 mmol) was added to a solution of 1-(6-chloro-pyridin-3-yl)-propan-1-one (2.8 g, 16.5 mmol) in methanol (70 mL) and the reaction mixture was heated under reflux for eighteen hours. The solution was concentrated to fifty percent, diluted with water (100 mL) and extracted with ethyl acetate (2×100 mL). The combined extracts were washed with brine, dried (Na$_2$SO$_4$) and concentrated to give product as a colorless oil (2.1 g, 77 percent yield), which was used without further purification.

Preparation of 1-(6-Chloro-pyridin-3-yl)-propan-1-one

To a solution of 6-chloro-N-methoxy-N-methyl nicotinamide (6.0 g, 30 mmol) (produced as disclosed in Perner, R. J. *J. Med. Chem.* 2003, 46, 5249) in THF (100 mL) was added a 3M solution of ethyl magnesium chloride in ether (15 mL, 45 mmol). The reaction mixture was heated under reflux for 4 hours and then stirred at approximately 25° C. for 14 hours. The reaction mixture was treated with a saturated aqueous solution of ammonium chloride (100 mL) and then extracted with ethyl acetate (2×100 mL). The combined extracts were washed with brine, dried (Na$_2$SO$_4$) and concentrated. The residue was purified by chromatography over silica gel, eluting with 10 percent ethyl acetate in hexane to give product as a white solid. (2.8 g, 60 percent yield).

Preparation of 1-[6-(2-Fluoroethoxy)pyridin-3-yl]ethanone (Compound 195)

2-Fluoroethanol (8.3 mol) was added to a solution of NaH (60 percent dispersion in oil, 8.3 mmol) in DMSO (6 mL) at approximately 25° C. After 30 minutes, a solution of 6-(chloropyridin-3-yl)ethanone (1.0 g, 6.4 mmol) in DMSO (5 mL) was added. Upon complete addition, the mixture was stirred at approximately 25° C. overnight. The mixture was quenched with water and extracted with Et$_2$O. The organics were combined, washed with brine, dried over anhydrous MgSO$_4$, and concentrated in vacuo, affording 640 mg of a yellow brown semi-solid.

The following compounds were prepared according to the procedure for Compound 195, using the appropriate alcohol: 1-[6-(2,2-Difluoroethoxy)pyridin-3-yl]ethanone (compound 194); 1-[6-(2,2,2-Trifluoroethoxy)pyridin-3-yl]ethanone (compound 175); and 1-[6-(methoxy)pyridin-3-yl]ethanone (compound 171).

Preparation of trans-1-[2-(4-Methoxybenzyloxymethyl)cyclopropyl]ethanone (Compound 201)

To a solution of trans-1-[2-(hydroxymethyl)cyclopropyl]ethanone (3.4 g, 30 mmol) (prepared as disclosed in Cossy, J.; Blanchard, N.; Meyer, C. *Eur. J. Org. Chem.* 2001, 339) in anhydrous DMF (60 mL) was added sodium hydride (60 percent dispersion in oil, 1.4 g, 36 mmol) in portions under N$_2$ at 0° C. After the addition was complete, the mixture was stirred for 25 minutes and 4-methoxybenzyl chloride (5.2 g, 33 mmol) was added in one portion. The reaction was then allowed to warm to approximately 25° C. and stirred overnight. The reaction was quenched with saturated aqueous ammonium chloride solution (30 mL) followed by dilution with water and was extracted with ether (4×50 mL). The combined organic layer was then washed with half-saturated brine and dried over $Na_2SO_4$. After filtration and concentration, the residue was purified on silica gel (20 percent acetone/hexane) to give 4.1 g of product as a colorless oil in 58 percent yield.

The following compound was prepared using methyl iodide according to the procedure used in preparing Compound 201: trans-1-[2-(methoxymethyl) cyclopropyl]ethanone (compound 198)

Preparation of trans-1-[2-(4-Methoxyphenoxymethyl)cyclopropyl]ethanone (Compound 202)

To a solution of trans-1-[2-(4'-methylsulfonyloxymethyl) cyclopropyl]ethanone (1.15 g, 6 mmol) and 4-methoxyphenol (1.15 g, 6 mmol) in dry DMSO (15 mL) was added potassium carbonate solid (0.89 g, 7.2 mmol) and the mixture was stirred at approximately 25° C. overnight. The mixture was then heated with a heat gun for a few minutes and then was continued to stir at approximately 25° C. for 3 hours. Water was added to the reaction mixture which was extracted with ether three times. The combined organic layer was washed with 2N NaOH aqueous solution and brine, dried over $Na_2SO_4$, filtered, concentrated, and purified on silica gel (30 percent acetone/hexane) to give a pale yellow oil (0.55 g) in 41 percent crude yield.

Preparation of trans-1-[2-(4'-Methylsulfonyloxymethyl)cyclopropyl]ethanone

To a solution of trans-1-[2-(hydroxymethyl)cyclopropyl] ethanone (3.2 g, 28 mmol) (produced as disclosed in Cossy, J.; Blanchard, N.; Meyer, C. *Eur. J. Org. Chem.* 2001, 339) and triethylamine (4.7 mL, 33.6 mmol) in $CH_2Cl_2$ (50 mL) was added methylsulfonyl chloride (2.6 mL, 33.6 mmol) at 0° C. under stirring. The mixture was stirred at approximately 25° C. overnight and then washed with $NaHCO_3$ solution, dried over $Na_2SO_4$, filtered, and concentrated to give 4.4 g of the crude product in 81 percent yield as a light brown oil.

The following compound was prepared using trifluoroethanol according to the procedure for Compound 202: trans-1-[2-(2,2,2-trifluoroethoxymethyl) cyclopropyl]ethanone (compound 203)

Preparation of 1,2,2,3,3,4,4,5,5,6,6-undecafluoroclohexanecarboxylic Acid 4-[2-(5-chlorothieno[2,3-d] pyrimidin-4-ylamino)ethyl]phenyl Ester (Compound 9a)

4-[2-(5-Chlorothieno[2,3-d]pyrimidin-4-ylamino)ethyl] phenol (15 g (0.0005 m)) and 0.3 g (~0.001 m) perfluoro cyclohexane carbonyl fluoride were suspended in 30 mL dichloromethane, and 0.3 g (excess) anh. pyridine was added with stirring; until all dissolved. After 1 hr. TLC ($SiO_2$-ether-lhexane) showed single major product spot and trace impurities. The product was rotovaped, redissolved in dichloromethane, washed with dil. HCl to pH 4-6, separated, and the acidic layer re-extracted with dichloromethane. The extract was combined with the original dichloromethane layer. The organic layer was washed with dil. ammonium hydroxide (pH 8-9), separated and the organic layer was filtered and rotovaped to obtain 0.33 g of a dark brown oil. The oil was dissolved in minimum ether, adding hexane while boiling off the ether. The product was filtered and the filtrate rotovaped to obtain 0.25 g of an orange oil. NMR (H and F) confirmed, but TLC still showed polar impurity. The product was boiled up in 2-methyl butane, filtered, and rotovaped to obtain 0.22 g of a dark yellow oil. M/Z=613.

Preparation of {4-[2-(5-chlorothieno[2,3-d]pyrimidin-4-ylamino)ethyl]phenyl}carbamic Acid t-butyl Ester (Compound 10a)

Step 1 A solution of 4-aminophenethylamine (0.41 g, 3 mmol) in THF (20 mL) was added to slurry of 4,5-dichlorothieno[2,3]pyrimidine (0.62 g, 3 mmol) and potassium carbonate in THF (40 mL) and the reaction heated at 100° C. for 2 minutes. After cooling, the solids were removed by filtration and the mother liquor concentrated in vacuo leaving a solid residue (1.3 g). This solid was dissolved in ether/ethyl acetate and washed with dilute aqueous sodium hydroxide. The organic phase was then extracted twice with dilute hydrochloric acid. The acidic extracts were combined, washed with ether/hexane, and the pH raised to 9 with aqueous sodium hydroxide. The resulting cloudy suspension was extracted exhaustively with ether and the combined organic portions filtered to give a clear yellow solution. Removal of solvent in vacuo gave product as a yellow solid, 0.58 g, 1.9 mmol, 64 percent yield. m.p. 154-7° C.

Step 2 Di-t-butylcarbonate (0.3 g, 1.4 mmol) was added to a solution of the above product (0.17 g, 0.56 mmol) in THF (15 mL) and the reaction heated at reflux for 1.5 h. After cooling, the solvent was removed in vacuo and the brown oil residue (0.33 g) purified by chromatography on silica eluting with ether. The product was isolated as a pale yellow foam, 0.15 g, 0.37 mmol, 66 percent yield.

Preparation of 1-[4-(2-aminoethyl)phenoxy]acetone (Compound 205)

Step 1 Chloroacetone (139 mg, 1.5 mmol) and potassium carbonate (260 mg, 1.9 mmol) were added to a solution of tert-butyl 2-(4-hydroxyphenyl)ethylcarbamate (308 mg, 1.3 mmol) in acetone (4 mL). The reaction mixture was heated to reflux for 16 h, cooled and solvent removed in vacuo. The residue was dissolved in $Et_2O$ and then washed with water and brine. The organics were dried ($Na_2SO_4$) and filtered through a bed of silica gel eluting with ether. The solvent was stripped off and the residue (~500 mg) was purified via flash chromatography eluting with 50 percent $Et_2O$ in pentane yielding off white solid, 256 mg, 0.87 mmol, 69 percent yield MS=293.

Step 2 Trifluoroacetic acid (0.56 mL, 7.3 mmol) was added to a solution of tert-butyl 2-[4-(2-oxopropoxy)phenyl]ethylcarbamate (216 mg, 0.74 mmol) in $CH_2Cl_2$ (4 mL). The reaction mixture was stirred for 3 hr at ambient temperature, and then reaction mixture was stripped of volatiles in vacuo. The residue (143 mg) was used without further purification.

2-(4-Morpholin-4-yl-phenyl)ethylamine (Compound 206)

Step 1 A solution of 2-[2-(4-bromophenyl)ethyl]-1H-isoindole-1,3(2H)-dione (0.5 g, 1.5 mmol) in dioxane (3 ml) was charged with morpholine (330 mg, 3.8 mmol), BINAP (47 mg, 0.08 mmol), and $Cs_2CO_3$ (1.4 g, 4.2 mmol). After brief nitrogen purge, $Pd(OAc)_2$ (9 mg, 0.004 mmol) was added and the reaction was heated at reflux for 24 h. After cooling, the reaction was diluted with ether, filtered through silica gel, and the filtrate was washed with $H_2O$ and dried ($Na_2SO_4$). Filtration and removal of solvent in vacuo left a residue that was purified by flash chromatography, eluting with 40 percent ether in pentane. Product isolated as a solid, 212 mg, 0.63 mmol, 42 percent yield. MS=336

Step 2 A solution of 2-[2-(4-morpholin-4-ylphenyl)ethyl]-1H-isoindole-1,3(2H)-dione (193 mg, 0.57 mmol) and hydrazine monohydrate (70 mg, 1.4 mmol) in ethanol (6 ml) was heated at reflux for 2 hr. The reaction was cooled to ambient temperature, and the solvent was removed in vacuo. The residue was taken up in ether, washed with 2M aqueous sodium hydroxide, and then extracted with 1M aqueous hydrochloric acid (2×10 mL). The acidic extracts were combined and the pH raised to 10-11 with 4M aqueous sodium hydroxide. This was then extracted thrice with ether, the organics combined, and dried ($Na_2SO_4$). Filtration and removal of solvent in vacuo left a brown oil, 110 mg, 0.57 mmol, 100 percent crude yield. The material was used without further purification.

The compounds of the present invention have been found to have significant fungicidal effect particularly for agricultural use. Many of the compounds are particularly effective for use with agricultural crops and horticultural plants.

In particular, the compounds effectively control a variety of undesirable fungi that infect useful plant crops. Activity has been demonstrated for a variety of fungi, including for example the following representative fungi species: Anthracnose of Cucumber (*Collatotrichum lagenarium*—COLLLA); Spot Blotch of Wheat (*Cochliobolus sativus*—COCHSA), Rice blast (*Magnaporthe grisea*—PYRIOR), Late Blight of Tomato and Potato (*Phytophthora infestans*—PHYTIN); Brown Rust of Wheat (*Puccinia recondita tritici*—PUCCRT); Powdery Mildew of Wheat (*Erysiphe graminis*—ERYSGT); Powdery Mildew of Cucumber (*Erysiphe cichoracearum*—ERYSCI); Leaf Blotch of Wheat (*Septoria tritici*—SEPTTR); and Glume Blotch of Wheat (*Septoria nodorum*—LEPTNO).

It will be understood by those in the art that the efficacy of the compounds against the foregoing fungi establishes the general utility of the compounds as fungicides.

Biological Testing

The activity of the compounds as effective fungicides was determined by applying the compounds to plants and observing control of fungal disease. The compounds were formulated at 200 ppm in 10 vol. percent acetone plus 90 vol. percent Triton X water (deionized water 99.99 wt. percent+0.01 wt. percent Triton X100), giving a "formulated test compound." In a few cases, compounds were formulated at 100, 75 or 8.3 ppm rather than 200 ppm in 10 vol. percent acetone plus 90 vol. percent Triton X water (deionized water 99.99 wt. percent+0.01 wt. percent Triton X100), giving a 'formulated test compound'. The compounds were tested for ability to control plant diseases in a 1-day protectant test (1DP) or a 2-day curative test (2DC). Formulated test compounds were applied to plants using a turn table sprayer fitted with two opposing air atomization nozzles which delivered approximately 1500 L/ha of spray volume. Plants were inoculated with spores of the fungus the next day (1DP), then incubated in an environment conducive to disease development. In a few cases, the compounds were tested for ability to control plant disease in a two-day curative test. Plants were inoculated with spores of the fungus two days prior to compound application, and incubated in an environment conducive to disease development both before and after compound application (2DC). For all types of tests, disease severity was evaluated 4 to 28 days later, depending on the speed of disease development.

The following experiments were performed in the laboratory to determine the fungicidal efficacy of the compounds of the invention.

Leaf Rust of Wheat (causal agent *Puccinia recondita tritici*=*Puccinia triticina*; Bayer code PUCCRT): Wheat plants (variety Yuma) were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit spores to germinate and infect the leaf. The plants were then transferred to a greenhouse until disease developed on untreated control plants.

Spot Blotch of Wheat (causal agent *Cochliobolus sativus*=*Bipolaris sorokineana*; Bayer code COCHSA): Wheat plants (variety Yuma) were grown from seed in a soil-less peat-based potting mixture (Metromix) until the seedlings had a fully expanded first leaf. Each pot contained 3-8 seedlings. These plants were sprayed until wet with the formulated test compound. On the following day, the leaves were inoculated with an aqueous spore suspension of *Cochliobolus sativus* and the plants were kept in high humidity for one to two days to permit spores to germinate and infect the leaf. The plants were then transferred to a greenhouse until disease developed on untreated control plants.

Cucumber Anthracnose (causal agent *Colletotricum lagenarium*; Bayer code COLLLA): Cucumber plants (variety Bush Champion) were grown from seed in a soil-less peat-based potting mixture (Metromix) until the first true leaf was 20-80 percent expanded. Each pot contained 1 seedling. These plants were sprayed until wet with the formulated test compound. On the following day, the leaves were inoculated with an aqueous spore suspension of *Colletotricum lagenarium* and the plants were kept in high humidity for one day to permit spores to germinate and infect the leaf. The plants were then transferred to a growth chamber until disease developed on untreated control plants.

Cucumber Powdery Mildew (causal agent *Erysiphe cichoracaerum*; Bayer code ERYSCI): Cucumber plants (variety Bush Champion) were grown from seed in a soil-less peat-based potting mixture (Metromix) until the first true leaf was 20-80 percent expanded. Each pot contained 1 seedling. These plants were sprayed until wet with the formulated test compound. On the following day, the leaves were inoculated with an aqueous spore suspension of powdery mildew spores (approximately 50,000 spores per milliliter). The plants were then incubated in a greenhouse until disease developed on untreated control plants.

Powdery Mildew of Wheat (causal agent *Erysiphe graminis* f. sp. *tritici*; Bayer code ERYSGT): Wheat plants (variety Yuma or Monon) were grown from seed in a soil-less peat-based potting mixture (Metromix) until the seedlings had a fully expanded first leaf. Each pot contained 3-8 seedlings. These plants were sprayed until wet with the formulated test compound. On the following day, the leaves were inoculated by dusting the leaves with leaves from plants heavily infected with *Erysiphe graminis* f. sp. *tritici*. The plants were then incubated in a greenhouse until disease developed on untreated control plants.

Glume Blotch of Wheat (causal agent *Leptosphaeria nodorum*=*Stagnospora nodorum*; Bayer code LEPTNO): Wheat plants (variety Yuma) were grown from seed in a 50 percent pasteurized soil/50 percent soil-less mix until the seedlings had a fully expanded first leaf. Each pot contained 3-20 seedlings. These plants were sprayed until wet with the formulated test compound. On the following day, (or two days before application for a two-day curative test), the leaves were inoculated with an aqueous spore suspension of *Lep-* tosphaeria nodorum and the plants were kept in high humidity (one day in a dark dew chamber followed by four to seven days in a lighted dew chamber) to permit spores to germinate and infect the leaf. The plants were then transferred to a greenhouse until disease developed on untreated control plants.

Tomato Late Blight (causal agent *Phytophthora infestans*; Bayer code PHYTIN): Tomato plants (variety Outdoor Girl or Rutgers) were grown from seed in a soil-less peat-based potting mixture (Metromix) until the second true leaf was 30-100 percent expanded. Each pot contained 1 seedling. These plants were sprayed until wet with the formulated test compound. On the following day, the leaves were inoculated with an aqueous suspension of *Phytophthora infestans* sporangia and zoospores, and the plants were kept in high humidity for one day to permit sporangia and zoospores to germinate and infect the leaf. The plants were then transferred to a growth chamber until disease developed on untreated control plants.

Rice Blast (causal agent *Magnaporthe grisea=Pyricularia oryzae*; Bayer code PYRIOR): Rice plants (variety M202) were grown from seed in a soil-less peat-based potting mixture (Metromix) until the seedlings had a partly to fully expanded second leaf. Each pot contained 5-20 seedlings. These plants were sprayed until wet with the formulated test compound. On the following day, the leaves were inoculated with an aqueous spore suspension of *Pyricularia oryzae* and the plants were kept in high humidity overnight to permit spores to germinate and infect the leaf. The plants were then transferred to a growth chamber at 22-24C until disease developed on untreated control plants.

Speckled Leaf Blotch of Wheat (*Mycosphaerella graminicola=Septoria tritici*; Bayer code SEPTTR): Wheat plants (variety Monon or Yuma) were grown from seed in a greenhouse in 50 percent pasteurized soil/50 percent soil-less mix until the first true leaf was fully expanded, with 3-8 seedlings per pot. These plants were sprayed until wet with the formulated test compound. On the following day, (or two days before application for a two-day curative test), the leaves were inoculated with an aqueous spore suspension of *Septoria tritici* and the plants were kept in high humidity (one day in a dark dew chamber followed by four to seven days in a lighted dew chamber) to permit spores to germinate and infect the leaf. The plants were then transferred to a greenhouse until disease developed on untreated control plants.

The following table presents the activity of typical compounds of the present invention when evaluated in these experiments. The effectiveness of the test compounds in controlling disease was determined by assessing the severity of disease on treated plants, then converting the severity to percent control based on the level of disease on untreated, inoculated plants.

TABLE 4: Activity of compounds as fungicides. Data are the level at which the given disease was controlled when the given compound was applied to the foliage of the plant at 200 ppm. In a few cases (noted in the table) the compound was applied to the plant at 100, 75 or 8.3 ppm. The plant was inoculated with the fungus one day after treatment. In a few cases (noted in the table) the plant was inoculated with the fungus two days before treatment.

TABLE 4

|    | COCHSA | COLLLA | ERYSCI | ERYSGT | LEPTNO | PHYTIN | PUCCRT | PYRIOR | SEPTTR |
|----|--------|--------|--------|--------|--------|--------|--------|--------|--------|
| 1  | *      | *      | NT     | ***    | ***    | **     | ***    | ***    | NT     |
| 2  | *      | *      | NT     | ***    | ***    | ***    | ***    | ***    | ***    |
| 3  | *      | *      | NT     | ***    | ***    | ***    | ***    | ***    | ***    |
| 4  | NT     | *      | ***    | **     | *      | NT     | ***    | ***    | **     |
| 5  | NT     | *      | ***    | **     | **     | NT     | ***    | **     | ***    |
| 6  | NT     | NT     | ***    | *      | **     | NT     | ***    | **     | **     |
| 7  | **     | *      | ***    | ***    | **     | ***a   | ***    | ***    | **     |
| 8  | NT     | *      | *      | *      | *      | *      | **     | **     | *      |
| 9  | ***    | *      | ***    | *      | **     | ***    | ***    | ***    | *      |
| 10 | NT     | *      | *      | *      | *      | *      | *      | **     | *      |
| 11 | *      | *      | *      | *      | **     | *      | **     | **     | **     |
| 12 | *      | *      | *      | *      | **     | ***    | **     | ***    | *      |
| 13 | *      | *      | *      | *      | *      | *      | *      | **     | *      |
| 14 | *      | ***    | ***    | ***    | ***    | ***    | ***    | ***    | ***    |
| 15 | *      | *      | *      | *      | *      | *      | ***    | **     | *      |
| 16 | **     | *      | *      | *      | *      | *      | *      | **     | *      |
| 17 | **     | *      | *      | *      | *      | *      | *      | *      | *      |
| 18 | *      | *      | ***    | ***    | ***    | ***    | ***    | ***    | ***    |
| 19 | ***    | *      | *      | **     | **     | *      | **     | ***    | **     |
| 20 | *      | NT     | *      | *      | *      | NT     | *      | *      | **     |
| 21 | *      | NT     | **     | *      | *      | NT     | ***    | ***    | **     |
| 22 | *      | NT     | ***    | *      | *      | NT     | ***    | ***    | **     |
| 23 | NT     | *      | ***    | NT     | *      | *      | ***    | **     | NT     |
| 24 | NT     | *      | *      | NT     | *      | *      | *      | **     | NT     |
| 25 | NT     | *      | ***    | NT     | ***    | ***    | ***    | ***    | NT     |
| 26 | NT     | *      | ***    | NT     | ***    | *      | ***    | ***    | NT     |
| 27 | NT     | *      | ***    | NT     | **     | *      | ***    | ***    | NT     |
| 28 | *      | NT     | NT     | *      | ***    | NT     | ***    | ***    | ***    |
| 29 | *a     | *      | ***    | ***a   | ***    | ***    | ***    | ***    | **a    |
| 30 | *      | *      | ***    | *      | *      | *      | ***    | ***    | *      |
| 31 | *      | *      | ***    | *      | *      | ***    | ***    | ***    | *      |
| 32 | *      | *      | *      | *      | *      | *      | ***    | ***    | *      |
| 33 | *      | *      | *      | *      | *      | *      | *      | **     | *      |
| 34 | *      | **     | ***    | ***    | ***    | *      | ***    | ***    | **     |
| 35 | *      | ***    | **     | *      | **     | **     | ***    | ***    | **     |
| 36 | *      | *      | *      | *      | *      | ***    | ***    | ***    | **     |
| 37 | *      | *      | ***    | **     | ***    | *      | ***    | ***    | *      |
| 38 | *      | *      | ***    | ***    | **     | ***    | ***    | ***    | **     |
| 39 | *      | *      | ***    | ***    | ***    | **     | ***    | ***    | ***    |

TABLE 4-continued

| | COCHSA | COLLLA | ERYSCI | ERYSGT | LEPTNO | PHYTIN | PUCCRT | PYRIOR | SEPTTR |
|---|---|---|---|---|---|---|---|---|---|
| 40 | ** | NT | NT | NT | ** | NT | *** | NT | NT |
| 41 | ** | * | *** | *** | *** | *** | *** | *** | *** |
| 42 | * | * | *** | ** | ** | * | *** | *** | *** |
| 43 | * | * | NT | NT | * | * | ** | ** | NT |
| 44 | ** | * | *** | * | ** | ** | *** | *** | * |
| 45 | * | * | *** | *** | ** | *** | *** | *** | ** |
| 46 | * | * | ** | NT | ** | * | *** | *** | NT |
| 47 | * | * | * | NT | ** | * | *** | *** | NT |
| 48 | *** | * | * | NT | * | * | * | * | NT |
| 49 | ** | * | NT | NT | * | * | *** | *** | NT |
| 50 | ** | * | NT | NT | * | * | * | * | NT |
| 51 | * | NT | NT | NT | * | NT | * | NT | * |
| 52 | * | * | NT | NT | * | * | * | * | ** |
| 53 | ** | * | NT | NT | * | * | *** | ** | ** |
| 54 | * | * | NT | NT | ** | *** | *** | *** | ** |
| 55 | * | * | NT | NT | ** | *** | *** | ** | *** |
| 56 | * | * | * | NT | * | * | ** | * | NT |
| 57 | * | * | ** | NT | * | * | *** | *** | *** |
| 58 | * | ** | * | NT | * | * | *** | *** | ** |
| 59 | * | * | ** | NT | * | * | *** | *** | ** |
| 60 | * | *** | *** | NT | * | * | *** | *** | * |
| 61 | ** | * | *** | NT | *** | * | *** | ** | ** |
| 62 | * | * | *** | NT | * | * | *** | *** | ** |
| 63 | NT | * | *** | ***a | ** | ** | *** | *** | NT |
| 64 | NT | * | * | NT | * | * | *** | *** | NT |
| 65 | NT | * | *** | *a | * | *** | *** | * | NT |
| 66 | NT | * | *** | ***a | * | ** | *** | *** | NT |
| 67 | NT | * | * | NT | * | * | *** | * | NT |
| 68 | NT | * | *** | NT | ** | ** | *** | *** | NT |
| 69 | NT | * | * | NT | **a, b | * | * | * | **a, b |
| 70 | NT | * | * | NT | * | * | * | ** | NT |
| 71 | NT | * | ** | NT | * | * | *** | * | NT |
| 72 | NT | * | *** | NT | * | * | *** | *** | NT |
| 73 | NT | *** | *** | NT | ** | * | *** | *** | NT |
| 74 | NT | *** | *** | NT | *** | * | *** | *** | NT |
| 75 | NT | ** | *** | NT | * | * | *** | *** | NT |
| 76 | NT | **a | NT | *a | NT | ***a | ***a | NT | NT |
| 77 | NT | **a | NT | *a | NT | ***a | ***a | NT | NT |
| 78 | NT | ***a | NT | ***a | NT | ***a | ***a | NT | NT |
| 79 | NT | * | * | NT | * | * | *** | *** | NT |
| 80 | NT | ** | *** | NT | * | * | *** | *** | NT |
| 81 | NT | NT | NT | NT | NT | NT | ***a | NT | NT |
| 82 | NT | * | *** | NT | * | * | *** | NT | NT |
| 83 | NT | * | *** | NT | * | * | *** | NT | NT |
| 84 | NT | NT | NT | NT | NT | NT | ***a | NT | NT |
| 85 | NT | * | *** | NT | * | *** | *** | NT | NT |
| 86 | NT | *** | *** | NT | ** | * | *** | *** | NT |
| 87 | NT | * | *** | NT | * | * | *** | *** | NT |
| 88 | NT | * | * | NT | * | * | *** | *** | NT |
| 89 | NT | * | * | NT | * | * | * | ** | NT |
| 90 | NT | * | *** | NT | ** | * | *** | *** | NT |
| 91 | NT | **a | *** | NT | *** | **a | *** | *** | NT |
| 92 | NT | * | * | NT | * | * | * | *** | NT |
| 93 | NT | * | * | NT | * | * | * | *** | NT |
| 1a | NT | NT | NT | NT | **a | NT | ***a | NT | NT |
| 2a | NT | * | *** | NT | * | *** | *** | *** | NT |
| 3a | NT | * | *** | NT | * | * | *** | *** | NT |
| 4a | NT | * | * | NT | * | * | * | ** | NT |
| 5a | NT | ** | *** | NT | *** | *** | *** | *** | ***a |
| 6a | NT | ** | * | NT | ** | *** | *** | *** | *d |
| 7a | NT | ** | *** | NT | * | *** | *** | *** | NT |
| 8a | NT | NT | NT | NT | **a | NT | ***a | NT | NT |
| 9a | NT | * | * | NT | * | * | *** | *** | ***d |
| 10a | NT | * | * | NT | * | NT | * | ***c | ***d |

\* is 0-49 percent control of disease
\*\* is 50-79 percent control of disease
\*\*\* is 80-100 percent control of disease
NT is No Test
"a" indicates that compound was tested at 100 ppm instead of 200 ppm.
"b" indicates that compound was tested in a two-day curative test instead of a one-day protectant test.
"c" indicates that compound was tested at 8.3 ppm.
"d" indicates that compound was tested at 75 ppm.

We claim:

1. A compound of Formula (I):

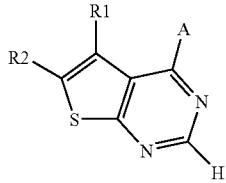
(I)

wherein R1 is selected from Cl, alkoxy, hydroxy, cyano, carbonylalkoxy, alkythio, and sulfonylalkyl;

R2 is selected from H, Cl, Br, F, I, $C_1$-$C_8$ alkyl, $C_3$-$C_8$ alkenyl, $C_3$-$C_8$ alkynyl, and carbonylalkoxy;

wherein A is NH—R"; and wherein R" is selected from the rings:

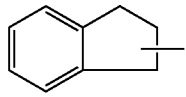
(II)

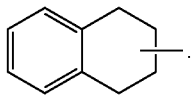
(III)

2. A compound of Formula (I):

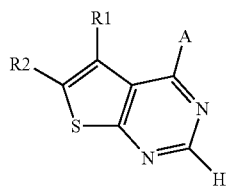
(I)

wherein R1 is selected from Cl, Br, F, I, $C_1$-$C_8$ alkoxy, hydroxy, cyano, carbonylalkoxy, alkythio, and sulfonylalkyl;

R2 is selected from H, Cl, Br, F, I, $C_1$-$C_8$ alkyl, $C_3$-$C_8$ alkenyl, $C_3$-$C_8$ alkynyl, and carbonylalkoxy, wherein A is 1,3-Dihydro-2H-isoindol-2-yl; and wherein the point of attachment is the N atom of the N-containing ring.

* * * * *